(12) United States Patent
Shehadeh

(10) Patent No.: US 8,754,059 B2
(45) Date of Patent: Jun. 17, 2014

(54) USE OF MIR-30E TO TREAT VASCULAR LESIONS

(75) Inventor: Lina Shehadeh, Coconut Creek, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 13/579,215

(22) PCT Filed: Feb. 16, 2011

(86) PCT No.: PCT/US2011/025005
§ 371 (c)(1),
(2), (4) Date: Aug. 15, 2012

(87) PCT Pub. No.: WO2011/103135
PCT Pub. Date: Aug. 25, 2011

(65) Prior Publication Data
US 2012/0308647 A1    Dec. 6, 2012

Related U.S. Application Data

(60) Provisional application No. 61/304,858, filed on Feb. 16, 2010.

(51) Int. Cl.
*A61K 48/00* (2006.01)
*C07H 21/02* (2006.01)
*C07H 21/04* (2006.01)

(52) U.S. Cl.
USPC .................. 514/44; 536/23.1; 536/24.5

(58) Field of Classification Search
CPC . C12N 15/113; C12N 2310/141; A61K 45/06
See application file for complete search history.

(56) References Cited

U.S. PATENT DOCUMENTS

2009/0203136 A1   8/2009   Baltimore
2009/0306181 A1   12/2009  Ikeda

OTHER PUBLICATIONS

International Search Report dated Jun. 28, 2011 for International Application No. PCT/US2011/025005, International Filing Date Feb. 16, 2011, consisting of 8 pages.
Anderson et al., MIR-206 Regulates Connexin43 Expression During Skeletal Muscle Development, Nucleic Acids Res., 2006, vol. 34, No. 20, pp. 5863-5871; abstract; Fig. 3B.

*Primary Examiner* — Amy Bowman
(74) *Attorney, Agent, or Firm* — Novak Druce Connolly Bove + Quigg LLP

(57) ABSTRACT

MicroRNA molecules are directed to the treatment of diseases associated with plaque formation, cardiovascular diseases, inflammation, stroke, and disorders associated with aging.

3 Claims, 15 Drawing Sheets

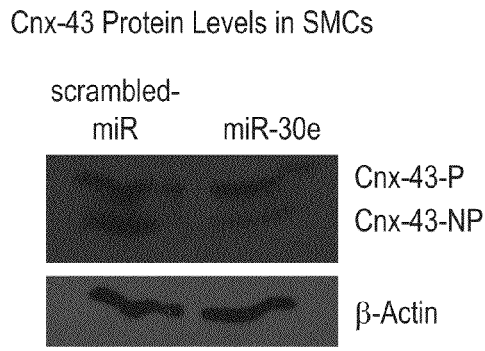
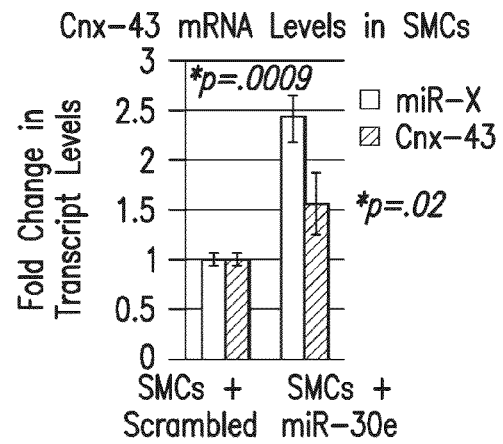
FIG.1A
FIG.1B
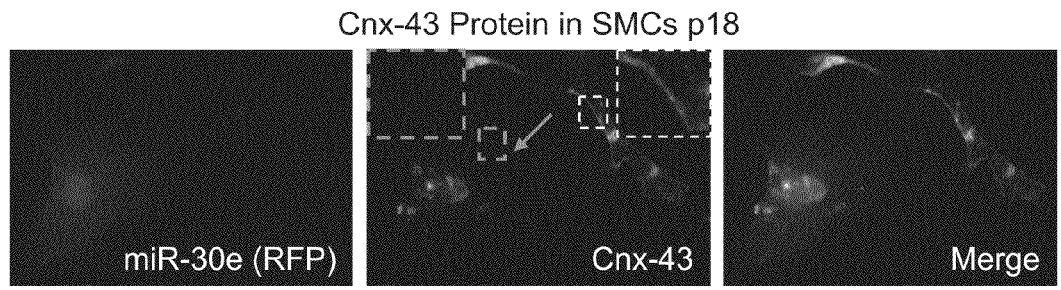
FIG.1C
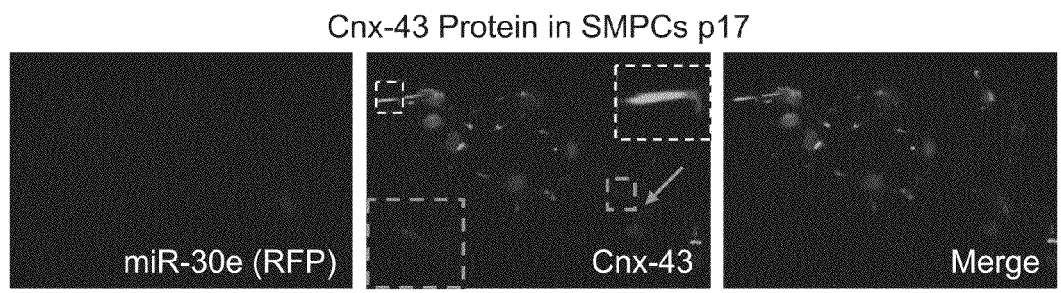
FIG.1D

Oil Red O Staining

Micro Ultrasound:

SEQUENCE LISTING

```
<160> NUMBER OF SEQ ID NOS: 3

<210> SEQ ID NO 1
<211> LENGTH: 20
<212> TYPE: RNA
<213> ORGANISM: HOMO SAPIENS

<400> SEQUENCE: 1
acacccacac acguacucgc                                              20

<210> SEQ ID NO 2
<211> LENGTH: 20
<212> TYPE: DNA
<213> ORGANISM: HOMO SAPIENS

<400> SEQUENCE: 2
tctgtgtatg tgaatgagcg                                              20

<210> SEQ ID NO 3
<211> LENGTH: 1731
<212> TYPE: RNA
<213> ORGANISM: HOMO SAPIENS

<400> SEQUENCE: 3
auacaggcuu gaaagcauca agauuccacu caauugugga gaagaaaaaa ggugcuguag    60
aaagugcacc aggguguuaau uuugauccgg uggagguggu acucaacagc cuuauucaug   120
aggcuugaaa acacaaagac auuagaauac cuagguucac ugggggugua uggguagau    180 gggugagag ggaggggaua agagaggugc auguugguau uuaaaguagu ggauucaaag    240
aacuuagauu auaaauaaga guuccauuag gugauacaua gauaagggcu uuuucucccc    300
gcaaacaccc cuaagaaugg uucuguguau gugaaugagc gggugguaau uguggcuaaa   360
uauuuuuguu uuaccaagaa acugaaauaa uucuggccag gaauaaauac uuccugaaca    420
ucuuaggucu uuucaacaag aaaaagacag aggauugucc uuaagucccu gcuaaaacau    480
uccauuguua aaauuugcac uuugaaggua agcuuucuag gccugacccu ccagguguca    540
auggacuugu gcuacuauau uuuuuuauuc uugguaucag uuuaaaaauuc agacaaggcc   600
```

```
cacagaauaa gauuuuccau gcauuugcaa auacguauau ucuuuuucca uccacuugca    660
caauaucauu accaucacuu uuucaucauu ccucagcuac uacucacauu cauuuaaugg    720
uuucuguaaa cauuuuuaag acaguuggga ugucacuuaa cauuuuuuuu uugagcuaaa    780
gucagggaau caagccaugc uuaauauuua acaaucacuu auaugugugu cgaagaguuu    840
guuuuguuug ucauguauug guacaagcag auacaguaua aacucacaaa cacagauuug    900
aaaauaaugc acauauggug uucaaauuug aaccuuucuc auggauuuuu gugguguggg    960
ccaauauggu guuuacauua uauaauuccu gcuguggcaa guaaagcaca cuuuuuuuuu   1020
cuccuaaaau guuuuucccu guguauccua uuauggauac ugguuuuguu aauuaugauu   1080
cuuuauuuuc ucuccuuuuu uuaggauaua gcaguaaugc uauuacugaa augaauuucc   1140
uuuuucugaa auguaaucau ugaugcuuga augauagaau uuuaguacug uaaacaggcu   1200
uuagucauua augugagaga cuuagaaaaa augcuuagag uggacuauua aaugugccua   1260
aaugaauuuu gcaguaacug guauucuugg guuuuccuac uuaauacaca guaauucaga   1320
acuuguauuc uauuaugagu uuagcagucu uuuggaguga ccagcaacuu ugauguuugc   1380
acuaagauuu uauuuggaau gcaagagagg uugaaagagg auucaguagu acacauacaa   1440
cuaauuuauu ugaacuauau guugaagaca ucuaccaguu ucuccaaaug ccuuuuuuaa   1500
aacucaucac agaagauugg ugaaaaugcu gaguaugaca cuuuucuucu ugcaugcaug   1560
ucagcuacau aaacaguuuu guacaaugaa aauuacuaau uuguuugaca uuccauguua   1620
aacuacgguc auguucagcu ucauugcaug uaauguagac cuaguccauc agaucaugug   1680
uucuggagag uguucuuuau ucaauaaagu uuuaauuuag uauaaacaua g            1731
```

USE OF MIR-30E TO TREAT VASCULAR LESIONS

CROSS REFERENCE TO RELATED APPLICATIONS

This Application is a §371 National Phase Entry of International Application No. PCT/US2011/025005, filed Feb. 16, 2011, entitled "THE USE OF MIR-30E TO TREAT VASCULAR LESIONS", which claims priority to U.S. Provisional Patented Application No. 61/304,858, filed Feb. 16, 2010, the entirety of which are incorporated herein by reference.

FIELD OF THE INVENTION

Embodiments of the invention provide microRNA molecules, compositions and methods for treatment of vascular lesions and protection against vascular lesions.

BACKGROUND

Almost one million Americans die from cardiovascular disease each year and atherosclerosis is the underlying cause of the majority of adverse events including myocardial infarct (MI) and stroke. While anti-atherosclerotic drugs exist, current treatments are sub-optimal and new approaches to treat atherosclerosis are needed.

Atherosclerosis is a progressive vascular disease characterized by endothelial dysfunction, upregulation of cell adhesion molecules, accumulation of lipids, macrophages, smooth muscle cells (SMCs), and fibrous tissue in the arterial intima. The process of atherogenesis is still not completely understood, but it is generally accepted that inflammation plays an important role in all stages of atherosclerosis.

Chronic inflammatory reactions in the arterial wall promote the recruitment of macrophages, SMCs, progenitor stem cells, monocytes and T lymphocytes in the arterial intima. This accumulation is regulated by the expression of cell adhesion molecules, including the gap junction protein Connexin 43 (Cnx-43) and chemokines including Cxcl5 which direct the migration of leukocytes and stem cells to vascular injury sites. These chemokines are essential components of atherogenesis. Thrombosis or embolism in a large atherosclerotic artery such as the aorta or carotid may cause MI or ischemic stroke.

Current non-surgical treatment regimes for atherosclerosis include: 1) statins and niacin that reduce circulating lipid levels, cholesterol and triglycerides. 2) wafarin, aspirin, and clopidogrel, anticoagulants and anti-platelet agents that reduce thrombosis.

SUMMARY

This Summary is provided to present a summary of the invention to briefly indicate the nature and substance of the invention. It is submitted with the understanding that it will not be used to interpret or limit the scope or meaning of the claims.

MicroRNAs (miRNAs or miRs) are a new class of regulatory RNAs that regulate the expression of families of genes and complex biological pathways. MiRNAs are under intense scrutiny as potential novel pharmacological agents for the treatments of complex disorders such as diabetes, arthritis and possibly atherosclerosis. A novel miRNA, miR-30e, was identified herein, that targets and represses the expression of adhesion, inflammation, migration and cholesterol-making molecules. This miRNA has a therapeutic potential for treating atherosclerotic carotid plaques.

Other aspects are described infra.

BRIEF DESCRIPTION OF THE DRAWINGS

FIG. 1A shows that miR-30e causes down-regulation of the non-phosphorylated Cnx-43. FIG. 1B shows that miR-30e causes over-expression of Cnx-43 transcript levels. FIGS. 1C-1D: From left to right, RFP positive (RFP+ve) red SMCs (FIG. 1C) and VPCs (FIG. 1D) over-expressing miR-30e show downregulated Cnx-43 expression, in green. Arrows point to the RFP$^+$ cells. Cnx-43 normally stains the outline of cells as in the RFP negative (RFP-ve ones. Nuclei are shown in blue.

DETAILED DESCRIPTION

Figure 2:
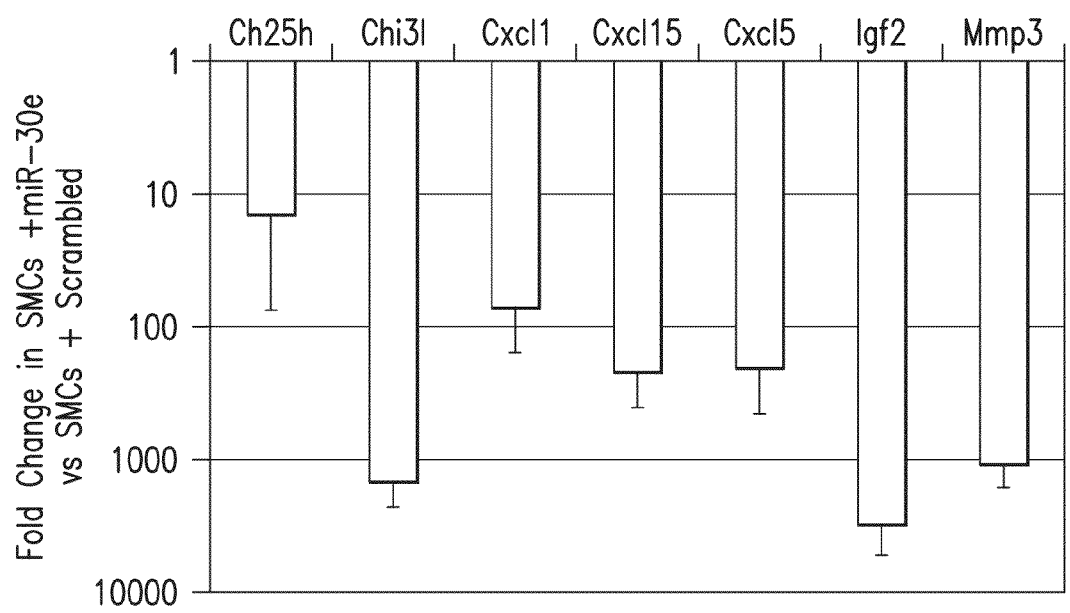
FIG. 2 is a graph showing the RT-PCR validation of genes downregulated by miR-30e in SMCs, including the steroid biosynthesizer Ch25h, athero adhesion factor Chi31, and 3 chemokines and insulin sensitivity gene Igf2 and the inflammation gene Mmp3. Y-axis: fold change.
Figure 3A:
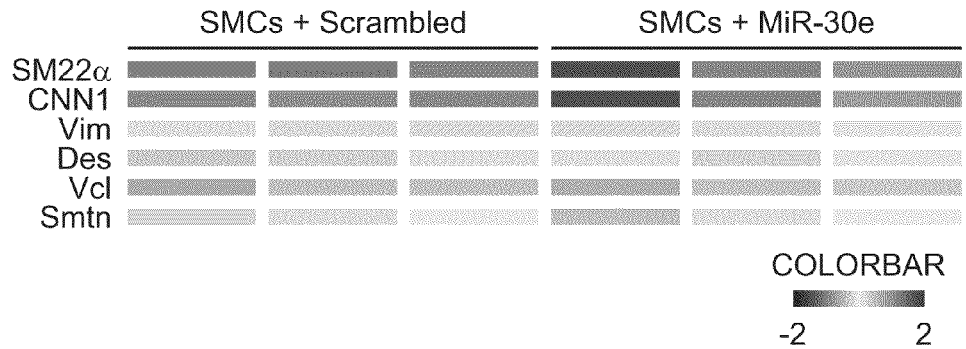
FIG. 3A: The gene expression data show significant induction of the smooth muscle markers Transgelin (Sm22β), Calponin (Cnn1), Vimentin (Vim), Desmin (Des), Vinculin (Vcl), and Smoothelin (Smtn) in SMCs over-expressing miR-30e relative to a scrambled oligonucleotide. Colorbar shows intensity in $Log_2$ scale.
Figure 3B:
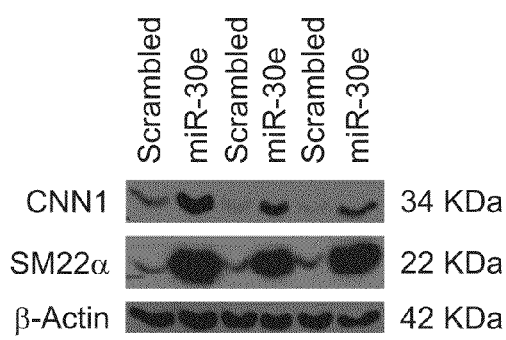
FIG. 3B: Calponin (CNN1) and Transgelin (SM22α) protein levels are highly induced in SMCs over-expressing miR-30e. β-actin was used as a loading control.
Figure 3C:
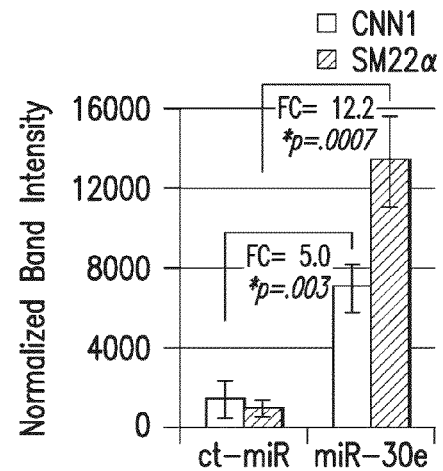
FIG. 3C: Densitometry shows that Cnn1 and Sm22a protein levels are significantly induced by 5 and 12 folds respectively.
Figure 3D:
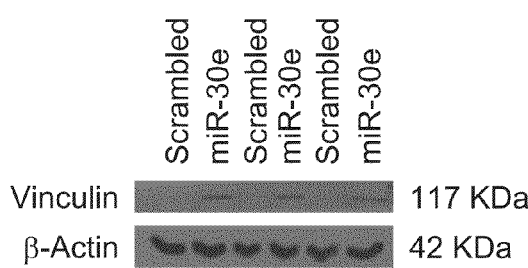
FIGS. 3D-3E: Similarly, Vinculin protein levels are significantly induced in SMCs over-expressing miR-30e.
Figure 3E:
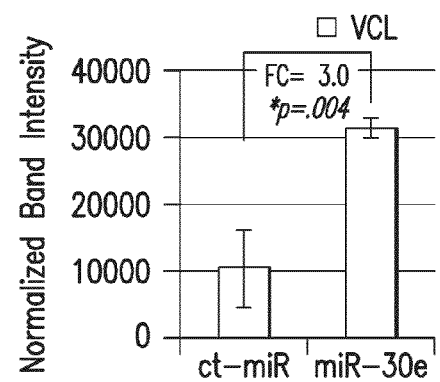

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"MicroRNA (miR)" is a small non coding RNA sequence that directs post transcriptional regulation of gene expression through interaction with a homologous mRNA. MiRs can inhibit translation, or can direct cleavage of target mRNAs. A microRNA is typically processed from pri-microRNA to short stem-loop structures called pre-microRNA and finally to mature miRNA. Both strands of the stem of the pre-microRNA may be processed to a mature microRNA.

When referring to a "target", what is meant is the target for an oligonucleotide of the invention. Typically, microRNA of the invention can interact with a target RNA by way of base pairing. The term "target" also encompasses DNA, RNA (comprising pre-mRNA and mRNA) transcribed from such DNA, and also cDNA derived from such RNA. The specific hybridization of an oligomeric compound with its target nucleic acid interferes with the normal expression, in vivo amounts and/or function of the nucleic acid. The functions of DNA to be modulated include, for example, replication and transcription. The functions of RNA to be modulated, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression, in vivo amounts, activity etc of an encoded product or oligonucleotides in vitro or in vivo.

When referring to "molecules associated with another molecule", this means any molecule that affects the expression, activity, function, physical or chemical properties in vivo or in vitro of a particular molecule. Thus a molecule that is associated with, for example, a cytokine will include any molecule involved in, for example, the synthesis, expression, activity, interaction with other molecules, and the like. This includes the nucleic acids (DNA or RNA) and peptides of that molecule, in this example, a cytokine.

"Reference level" or "control level", within the meaning of the invention, shall be understood as being any reference level with which a measured level of, e.g., expression or activity can be compared to. Such reference levels can be obtained, e.g., from previous experiments or from literature. "Wild-type level", with respect to an expression level of a gene, shall be understood as being an expression level typically observed in wild-type organisms, i.e. in not recombinantly modified organisms of the same species.

"Binding affinity" of a molecule A to a molecule P, within the meaning of the invention shall be understood as being the thermodynamic quantity that corresponds to the dissociation constant of the complex consisting of the molecule A and the molecule P in a reaction A+P→AP under standard conditions. In this case the binding affinity is [A]*[B]/[AB], wherein square brackets symbolize the concentration of the respective species.

As used herein, "modulation" means either an increase (stimulation) or a decrease (inhibition) in the expression, in vivo amounts, activity, function of a gene in vitro or in vivo as compared to normal controls. The term includes, for example, increased, enhanced, increased, agonized, promoted, decreased, reduced, suppressed blocked, or antagonized. Modulation can increase activity or amounts more than 1-fold, 2-fold, 3-fold, 5-fold, 10-fold, 100-fold, etc., over baseline values. Modulation can also decrease its activity or amounts below baseline values. For example, in patients these are compared to normal, physiological amounts, activity etc.

"Nucleic acids", within the meaning of the invention, shall be understood as being all known nucleic acids such as DNA, RNA, peptide nucleic acids, morpholinos, and nucleic acids with backbone structures other than phosphodiesters, such as phosphothiates or phosphoramidates. Non-naturally occurring nucleotides include nucleotides which have modified sugar moieties, such as bicyclic nucleotides or 2' modified nucleotides, such as 2' substituted nucleotides.

The term "nucleotide" as used herein, refers to a glycoside comprising a sugar moiety, a base moiety and a covalently linked phosphate group and covers both naturally occurring nucleotides, such as DNA or RNA, preferably DNA, and non-naturally occurring nucleotides comprising modified sugar and/or base moieties, which are also referred to as "nucleotide analogues" herein. "Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligomer, i.e. have no functional effect on the way the oligomer works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213

"Arteriosclerosis", within the meaning of the invention, is the thickening and hardening of the arteries due to the build-up of calcium deposits on the insides of the artery walls. Cardiovascular diseases, preferably disorders of lipid metabolism and atherosclerosis is a similar condition due to the build-up of fatty substances. Both conditions have similar effects on the circulation of the blood throughout the body. Heart disease, high blood pressure, stroke, and ischemia (starvation of the cells due to insufficient circulation) may be the result of arteriosclerosis and cardiovascular diseases, preferably disorders of lipid metabolism and atherosclerosis. Within the context of this invention, "Atherosclerosis" shall be understood as encompassing both, Atherosclerosis and Arteriosclerosis and stroke as defined above.

The term "biological sample" refers to a fluid, cell or tissue sample from a subject. Fluid samples include, but are not limited to saliva, tears, urine, whole blood, plasma, lymphatic fluid, interstitial fluid, and cerebrospinal fluid.

As used herein, the term "safe and effective amount" or "therapeutically effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, in vivo amounts, etc.).

A "stem cell" as used herein is an undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. For example, blood stem cells may become brain cells or liver cells, neural stem cells can become blood cells, such that stem cells are pluripotential, and given the appropriate signals from their environment, they can differentiate into any tissue in the body.

"Propagation" can be determined, for example, by the ability of an isolated stem cell to be propagated through at least 50, preferably 100, and even up to 200 or more cell divisions in a cell culture system. Stem cells can be "totipotent," meaning that they can give rise to all the cells of an organism as for germ cells. Stem cells can also be "pluripotent," meaning that they can give rise to many different cell types, but not all the cells of an organism. When a stem cell differentiates it generally gives rise to a more adult cell type, which may be a partially differentiated cell such as a progenitor cell, a differentiated cell, or a terminally differentiated cell. Stem cells can be highly motile.

"Isolating" a stem cell refers to the process of removing a stem cell from a tissue sample and separating away other cells which are not stem cells of the tissue. An isolated stem cell will be generally free from contamination by other cell types, i.e. "homogeneity" or purity" and will generally have the capability of propagation and differentiation to produce mature cells of the tissue from which it was isolated. An isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, 99%, or 99.9% pure. Preferably, isolated stem cells according to the invention will be at least 98% or at least 99% pure.

As used herein, "culturing" refers to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

MicroRNA (miRNA) Molecules

Compounds which antagonize adhesion molecules or chemokines also reduce the extent of atherosclerotic lesion. Such compounds include statins which are shown to reduce connexin-43 (Cnx-43) in atherosclerotic plaques and repress chemokine (C—X—C motif) ligand 5 (Cxcl5) levels in endothelial cells. Cnx-43 is upregulated in atherosclerotic plaques and so are the inflammation molecules matrix metalloproteinase-3 and 9 (Mmp3 and Mmp9) which initiate plaque disintegration. Mmp9 is highly associated with carotid plaque and is downregulated by statin in atherogenic APOE$^{-/-}$ mice. Statins might then exert their effect through mechanisms other than their lipid-lowering effects. Since atherosclerosis is a complex disorder, an optimized therapy should not be limited to one gene (and hence one pathway) within the atherogenic process, but rather should target multiple key genes that can more effectively repress entire biological pathways of atherogenesis. Since miRNAs have evolved to target multiple related genes within complex biological pathways, they hold enormous potential for the treatment of diseases such as atherosclerosis provided the key miRNAs can be identified.

In a preferred embodiment, an isolated microRNA molecule comprises between about ten to fifty moieties, wherein each moiety is bonded to each other, the microRNA molecule comprising a sequence which either directly or indirectly or specifically binds to one or more molecules to modulate the expression, function or activity of that molecule. The target sequence may be any sequence which is partially or perfectly complementary to the sequence of bases in a target molecule. For example, depending on the disease state that is desired for preventing or treating a patient, the microRNA molecules will be synthesized to be specific for the molecules that are associated with that disease. Thus, in another embodiment, the microRNA's can be tailored to each individual patient's need, for example, as in individualized medicine.

The microRNA can either bind to the complementary sequences on the target molecule, or it may directly affect the expression or function by modulating, for example, transcription, or it may function indirectly by modulating the activity, expression, or function of a molecule that may be associated with the target molecule's activity, function or expression. Since the mechanism of action of how the microRNA will modulate the target molecule's expression, function or activity, is beyond the scope of the disclosure, as long as the microRNA modulates the desired outcome, as for example, shown in the examples section which follows, the terms "specifically binds to", "directly or indirectly regulates" encompasses any known or heretofore unknown mechanisms and associated molecules involved in those expression, activities or functions of the target molecule without restriction.

The "modulation" of a desired or specific activity, or function or expression can be compared to a base line or other control. The term includes upregulation, no change and down regulation as compared to a baseline control. In a preferred embodiment, the microRNA modulates the expression, function, or activity of the target molecule by at least about 10% as compared to a baseline or other control, preferably at least about 20%, preferably at least about 40%, preferably at least about 50%, preferably at least about 75%, preferably at least about 80%, 90%, 99.99% or 100% as compared to a base line or other control.

In a preferred embodiment, the microRNA comprises the miR-30 family, variants, analogs, mutants, species, homologs, allelic variants or combinations thereof. In another preferred embodiment, the miR-30 family comprises miR-30a, miR-30b, miR-30c, miR-30d, and miR-30e.

In another preferred embodiment, an isolated microRNA molecule comprises between about ten to fifty moieties, the microRNA molecule comprising a sequence which specifically binds to complementary sequences on target messenger RNA transcripts (mRNAs) of molecules comprising: cell adhesion molecules, molecules associated with cell adhesion, molecules associated with inflammation, molecules associated with cholesterol, cholesterol, molecules associated with cell migration, chemokine molecules, chemokine modulating molecules, cytokines, molecules associated with osteogenesis, or collagen and collagen associated molecules. For example, administration of one or more microRNA molecules, e.g. miR30e, to a cell in vivo, downregulates connexin-43 expression. In other examples, miR30e induces expression of collagens (e.g. Col3a1, Col4a4, Col6a3); represses osteogenesis via major osteogenic transcription factors (Runx2, Bmp2, Spp1 and Postn); downregulates senescent markers (p21, p16). Thus, in some embodiments, modulation of expression, function or activity of target sequences can be identified. These molecules can be quantified for increase or decrease or no change in expression when contacted by the microRNA.

In another preferred embodiment, the microRNA binds to complementary sequences of 3' Untranslated Region (3' UTR) molecules. The data in the examples section which follows, it was found that genes belonging to the cell adhesion gene ontology biological function, such as Connexins and Thrombospondins, were upregulated in plaque lesions. By studying the 3'UTRs of these genes and an over-representation of a miR-30e binding site in these 3'UTRs were found, evidencing a common microRNA regulator for these adhesion genes. miR-30e was significantly downregulated in human failing hearts, in rodent vascular restenosis, and in human platelets during thrombin activation.

In another preferred embodiment the microRNA binds to target sequences which are partially or substantially complementary to the microRNA. As used herein, "partially complementary" refers to a sequence that is at least about 75%, 80%, 85%, 90%, 95%, 96%, 97%, 98%, or 99% complementary to a target polynucleotide sequence. In some embodiments, the microRNA is "substantially complementary" to a target sequence, that is at least about 90%, 95%, 96%, 97%, 98%, or 99% complementary.

In the case of diseases or disorders associated with plaque formation, the results herein, show that modulation of cell adhesion molecules can be used to treat such diseases or disorders. The administration of the microRNA, for example miR30e, results in changes of various molecules (see, for example, Example 1). Briefly, miR-30e not only downregulated by more than 10 fold (p<0.05) adhesion genes, but also inflammation (Mmp3 and Mmp9), cholesterol making and chemokine/migration genes, all key contributors to atherogenesis (FIG. 2). Downregulated by more than 100 fold was CXCL5, which is highly inducible in endothelial and vascular SMCs and is implicated as a marker in congestive heart failure and ischemic stroke. On the other hand, miR-30e upregulated the SMC lineage marker SM22α, evidencing that miR-30e drives the SMCs back to their quiescent differentiated state (FIG. 3). SM22α has an anti-calcification effect in SMCs. In support of an anti-calcification role for miR-30e, the microarrays data also show that miR-30e significantly downregulates the osteogenic transcription factors Runx2 and Bmp2, usually elevated in calcified atherosclerotic vessels.

Accordingly, in a preferred embodiment, microRNA molecules specifically modulate the expression, function or activity of one or more cell adhesion molecules or molecules associated with cell adhesion expression, function, or activity.

In another preferred embodiment, the isolated microRNA molecule comprises a sequence that is at least about 50% complementary to at least five consecutive nucleic acids of a 3' UTR of a cell adhesion molecule.

Non-limiting examples of cell adhesion molecules, comprise: molecules in the connexin families, chitinase 3-like 1 (CHI3L1), SFRP1 (secreted frizzled-related protein 1), matrix metallopeptidases, chemokines, growth factors, cholesterol modulating molecules, lipids, glycolipids, glycoproteins, sugars, integrins, selectins, the immunoglobulin superfamily, cadherins, proteoglycans, mucins, insulin sensitivity genes, fragments, mutants, variants, soluble or membrane forms thereof.

In a preferred embodiment, a molecule in a connexin family is connexin 43.

In another preferred embodiment, the chemokine molecules comprise: Cxcl1, Cxcl5, or Cxcl15.

In another preferred embodiment, the cholesterol modulating molecules comprise: apolipoproteins, glucagon, cAMP or Ch25h.

In another preferred embodiment, the insulin sensitivity genes comprise: insulin growth factor (Igf2) or intestinal fatty acid binding protein (FABP2) gene.

In another preferred embodiment, the microRNA molecules regulate the differentiation potential or differentiation of the stem cells. As used herein, "differentiation potential" refers to the different lineages that a stem cell can differentiate into. For example, osteogenic, adipogenic, chondrogenic, cardiogenic lineages, and the like. In one embodiment, the stem cells are pluripotent stem cells. In another embodiment, the stem cells are mesenchymal stem cells.

In another preferred embodiment, stem cells may be embryonic stem cells, adult stem cells, umbilical cord blood stem cells, somatic stem cells or cancer stem cells. In preferred embodiments, the stem cells are adult stem cells, preferably cardiac stem cells.

Additionally, the stem cells of the current invention may be hematopoietic stem cells, or mesenchymal stem cells. The stem cells of the current invention may be totipotent, pluripotent, multipotent or unipotent stem cells.

The stem cells of the current invention may be primary stem cells or may be derived from an established stem cell line, premalignant stem cell line, cancer cell line, or any cell line that manifests any stem cell marker. Primary stem cells may be derived from a cancer patient or a healthy patient.

In another preferred embodiment, a method of regulating the differentiation of stem cells comprising contacting a stem cell in vivo or in vitro with at least one microRNA molecule.

In a preferred embodiment, the stem cells are used in methods of repairing and/or regenerating damaged tissues or organs in a subject in need thereof by administering isolated stem cells to areas of damaged tissues or organs, wherein the administered stem cells differentiate into one or more cell types. The ability to restore both functional and structural integrity is yet another aspect of this invention. In a preferred embodiment, the stem cells are adult stem cells. In another embodiment, adult stem cells are isolated from the subject in need of therapeutic treatment and implanted back into the subject. Since the microRNA can regulate the differentiation potential of the stem cells, the stem cells can be contacted with the microRNA, be cultured and expanded ex vivo and administered to the patient. Alternatively, the microRNA can be administered to the patient via suitable routes. In other embodiments, a vector comprising the microRNA is used for both contacting cells in vitro or administration in vivo. In some embodiments of the invention, the isolated stem cells are differentiated prior to administration to a subject.

Thus, in preferred embodiments, the invention involves administering a therapeutically effective dose or amount of stem cells to the subject. An effective dose is an amount sufficient to effect a beneficial or desired clinical result. The dose could be administered in one or more administrations. The precise determination of what would be considered an effective dose may be based on factors individual to each patient, including their size, age, area of myocardial damage, and amount of time since damage. One skilled in the art, specifically a physician, would be able to determine the number of stem cells that would constitute an effective dose without undue experimentation.

In some embodiments, the administration of stem cells to a subject in need thereof is accompanied by the administration of one or more cytokines. The cytokines may comprise: stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), insulin-like growth factor-1 (IGF-1), Interleukin-3, or any cytokine capable of the stimulating and/or mobilizing stem cells. In a preferred embodiment, the cytokines are selected from HGF, IGF-1, functional variants of HGF or IGF-1, or combinations thereof. The cytokines may be delivered simultaneously with the stem cells. Alternatively, the administration of the cytokines may either precede or follow the administration of the stem cells by a specified time period. The time period may be about 15 minutes, about 30 minutes, about 1 hour, about 3 hours, about 6 hours, about 12 hours, about 24 hours, about 36 hours, about 1 week, about 2 weeks, about 1 month, or about 6 months.

In another preferred embodiment, the microRNA comprises a miR-30 family, variants, analogs, mutants, species, homologs, allelic variants or combinations thereof.

In another preferred embodiment, the miR-30 family comprises miR-30a, miR-30b, miR-30c, miR-30d, or miR-30e.

The microRNA molecules can be synthesized to incorporate different moieties such as modified nucleotides, analogs, etc. The linkages can between the moieties can be modified internucleoside linkages or backbones, etc. See, the discussion regarding the modifications below.

Accordingly, in another preferred embodiment, the moieties comprise: a nucleobase, a sugar moiety, a modified sugar moiety, a modified nucleobase, analogues or combinations thereof.

In one preferred embodiment, the modified sugar moiety comprises: a 2'-O-methoxyethyl modified sugar moiety, a 2'-methoxy modified sugar moiety, a 2'-O-alkyl modified sugar moiety, or a bicyclic sugar moiety.

In another preferred embodiment, modified nucleobases comprise peptide nucleic acids, locked nucleic acid (LNA) molecules, analogues, derivatives or combinations thereof.

In yet another preferred embodiment, the analogs comprise: 2'-MOE-RNA (2'-O-methoxyethyl-RNA), 2'Fluoro-DNA, LNA, and/or cholesterol moiety or combinations thereof.

In another preferred embodiment, the moieties are optionally linked by at least one modified internucleoside linkage. Examples of modified internucleoside linkages comprise: a phosphorothioate, alkylphosphonate, phosphorodithioate, alkylphosphonothioate, phosphoramidate, carbamate, carbonate, phosphate triester, acetamidate, carboxymethyl ester, or combinations thereof.

MicroRNAs and Atherosclerosis:

miRNAs are endogenous non-coding approximately 22 nucleotide RNAs that regulate gene expression at the post-transcriptional level. First reported 16 years ago, miRNAs belong to one of the largest gene families and account for ~1% of the genome. The miRNA database, MiRBase, currently lists 718 human miRNA sequences. More than 30% of the human genome is estimated to be under transcriptional control by miRNAs, although the number of validated targets remains small. MiRNA regulation is implicated in multiple processes of fundamental biological importance including cellular differentiation, proliferation, growth, metabolism and apoptosis. MiRNAs act by cleaving or translationally repressing mRNAs, thereby regulating the cellular levels of target proteins. Without wishing to be bound by theory, it is hypothesized that specific miRNAs exert powerful regulation over vascular integrity, for example, vascular neointimal lesion formation is regulated by a set of miRNAs that constitute a restenosis molecular genetic signature. In a related context, miRNAs regulate differentiation and pluripotency of embryonic stem cells and may be involved in the plasticity of multipotent cardiac progenitors that can differentiate into cardiac myocytes, cardiovascular disease remains unacceptably high despite years of research into small molecule drugs that target the blood and vasculature.

Cardiovascular disease costs the nation $274 billion each year. Novel therapeutic approaches are desperately needed. Traditional pharmacotherapy and life style changes can retard the progression of atherosclerosis in some subjects but they do not treat the root cause of plaque development.

In a preferred embodiment, miRNAs prevent or treat atherosclerosis. Preferably, the miRNAs simultaneously block multiple points in the pathways of plaque formation. Without wishing to be bound by theory, if under-expression of a single miRNA can cause the progression of atherosclerosis, augmentation of this miR would block atherosclerosis.

An important difference between miRNA therapy and traditional pharmacology is that current drug strategies have specific cellular targets whereas miRNAs can modulate the entire functional network. Consequently miR therapy is likely to be much more effective for complex conditions like atherosclerosis. As the data herein show, miR-30e targets key elements in the atherogenic pathway. In addition to their potent regulatory effects, synthetic miRNA oligonucleotides are stable in vivo for 2-3 months, and are not rejected by the host's immune system. In many pharmacological interventions including adenovirus mediated targeted gene delivery and stem cell delivery, immunogenic rejection can limit efficacy. This is not the case for miRNAs. The miRNAs will be used to develop novel therapeutics and the synergistic use of bioinformatics and molecular biology approaches taken here, are easily translated into clinical applications.

In a preferred embodiment, a method of preventing or treating a disease or disorder associated with plaque formation, comprises administering to a patient in need thereof, at least one microRNA molecule in therapeutically effective amounts which specifically bind to at least one cell adhesion molecule; down-regulating expression, function or activity of the cell adhesion molecule. Preferably, the microRNA molecules specifically bind to and modulate activity, expression or function of cell adhesion molecules, comprising: connexin families, chitinase 3-like 1 (CHI3L1), SFRP1 (secreted frizzled-related protein 1), matrix metallopeptidases, chemokines, growth factors, cholesterol modulating molecules, lipids, glycolipids, glycoproteins, sugars, integrins, selectins, the immunoglobulin superfamily, cadherins, proteoglycans, mucins, insulin sensitivity genes, fragments, mutants, variants, soluble or membrane forms thereof.

In a preferred embodiment, more than one microRNA molecule, each with a different specificity for the same molecule are administered to a patient. For example, if it is desired to specifically target a connexin 43 molecule, microRNA molecules with varying specificities can be used if desired. Each microRNA can, for example, target overlapping sequences. Each overlap can be as small as by one nucleotide.

In another preferred embodiment a disease or disorder associated with plaque formation comprises: cardiovascular diseases, atherosclerosis, high cholesterol, diabetes, disorders of lipid metabolism, neuroinflammatory diseases or disorders, neurological diseases or disorders, neurodegenerative diseases or disorders, kidney or urologic diseases or disorders, cancer, inflammation, or autoimmune diseases or disorders.

In another preferred embodiment, a method of preventing or treating atherosclerosis comprises administering to a patient in need thereof, at least one microRNA molecule in therapeutically effective amounts which specifically bind to at least one cell adhesion molecule; down-regulating expression, function or activity of the cell adhesion molecule; thereby, preventing or treating atherosclerosis.

The microRNA molecules can be administered to a patient via a stent, vector, liposome, lipid, sugar, or cell-penetrating complex.

MicroRNAs and Aging:

Aging is an independent risk factor for vascular disease. Animal experiments have demonstrated that aging predisposes the vasculature to vessel injury which is a function of age-associated changes in the vessel wall including the endothelium and smooth muscle layers. Vascular smooth muscle cells (VSMCs) are particularly implicated in the pathogenesis of many vascular disorders including atherosclerosis and restenosis. Identification of age-associated dysfunction or integrity of these cells and their responses to the vascular wall environment would lead to new therapeutic targets. Although vascular calcification can occur independently of atherosclerosis, in the majority of advanced atherosclerotic lesions, it contributes to the overall morbidity of atherosclerosis by decreasing the elasticity of the vessels, and is strongly age-dependent. Vascular calcification is accompanied by an accelerated transition of older VSMCs from an elastic collagen-rich phenotype of the younger cells to a calcified bone-like phenotype. Using a bioinformatics approach, a microRNA, miR-30e, was identified (see, the examples section which follows) that is dynamically regulated with age in mouse aortic SMCs. It was found that in vascular SMCs, miR-30e potently induced expression of collagens (Col3a1, Col4a4, and Col6a3), repressed osteogenesis via major osteogenic transcription factors (Runx2, Bmp2, Spp1, and Postn), and downregulated senescence markers (p21 and p16). Without wishing to be bound by theory, it was hypothesized that age-associated downregulation of miR-30e in SMCs induces vascular senescence and drives the transition of SMCs from the elastic/flexible to calcified/stiff phenotype with age. In preferred embodiments, miR-30e regulates expression, function, or activity of collagen expression in mouse aortic SMCs from young and old mice, and/or osteogenic differentiation of bone marrow-derived mesenchymal stem cells.

In another preferred embodiment, miR-30e regulates the collagen repressors IRF2 and GATA4, for example, in aging vascular smooth muscle cells (VSMCs). Collagens are downregulated during aging and members of transcription factors IRFs and GATAs repress collagen expression. The data herein show that miR-30e has binding sites in the 3' UTRs of GATA2 and IRF-4 and that over-expression of miR-30e in senescing VSMCs, down-regulates IRF2, GATA2, and GATA4, and upregulates a group of collagens. It was hypothesized that miR-30e regulates collagens indirectly by binding to their repressors.

In another preferred embodiment, miR-30e regulates of osteogenesis, for example, in mesenchymal stem cells (MSCs). Subpopulations of cells within the vascular smooth muscle can form osteoblasts, these may include vascular SMCs themselves, myofibroblasts and MSCs. It is hypothesized that aging induces calcification of blood vessels by activating osteogenic pathways in SMCs and MSCs. The data herein show that in SMCs, over-expression of miR-30e down-regulates Runx2, a transcription factor which drives MSC differentiation into a calcified/bone lineage.

Aging and Vascular Abnormalities.

Epidemiological studies have shown that aging is an independent risk factor for the development of vascular abnormalities such as atherosclerosis which plays a significant role in the development of many cardiovascular disorders. For example, increased vascular stiffness with aging represents an independent risk factor of myocardial ischemia and stroke. Animal experiments, in which genetic variations are minimized and exposure to atherosclerosis-inducing stimuli can be precisely controlled, support the notion that aging by itself predisposes the vasculature to advanced atherosclerotic disease. Together, these results indicate that the higher incidence and greater severity of vascular lesions in older animals are the result of biological changes in the organism related to aging.

Smooth Muscle Cells and Vascular Calcification with Age.

Vascular calcification is widespread in patients with coronary artery disease and peripheral artery disease and is closely associated with the incidence of cardiovascular events as well as all-cause mortality. Calcification in the tunica media (a layer of circumferential smooth muscle cells and collagen fibers) is often observed in elderly people and is highly correlated with their morbidity and mortality. It is likely that vascular calcification is regulated by the machinery similar to bone formation, and is accomplished through the extracellular matrix (ECM) calcification. During the ECM calcification hydroxyapatite crystals that contain calcium and inorganic phosphate precipitate within the collagen fibrils. Many key players in the ECM calcification, such as matrix G1a protein (MGP) and alkaline phosphatase (ALP), have been identified. ALP promotes ECM calcification by cleaving pyrophosphate. Osteoblasts play a central role in the ECM calcification by producing both ALP, a major component of the ECM in bone matrix, and Runx2, a transcription factor that activates the bone pathway. Bone calcification regulatory factors have been identified in blood vessels, particularly at sites of medial calcification and calcified atherosclerotic plaque. Calcification in the media can occur in the absence of macrophages and lipid and is associated with α-smooth muscle actin-positive vascular smooth muscle cells (SMCs), indicating the possible role of senescence of these cells as a component of medial calcification. However, it remains unclear what induces the altered expression of the Runx2 in the calcified vessels or how vascular SMCs are involved in the formation of senescence-associated medial calcification. As the population ages, senescence-associated medial calcification is becoming an increasingly prominent clinical threat. However, little is known about the molecular mechanisms governing medial calcification. The degree of involvement of cellular senescence in vascular SMCs in the formation of medial calcification is still unclear. In addition, it remains to be determined whether pharmacological intervention can prevent or reverse the vascular SMC calcification associated with senescence.

microRNAs and Smooth Muscle Cells.

More than 30% of the human genome is estimated to be under transcriptional control by miRs, although the number of validated targets remains small. MicroRNA regulation is implicated in multiple processes of fundamental biological importance including cellular differentiation, proliferation, growth, metabolism and apoptosis. MiRNAs act by cleaving or translationally repressing mRNAs, thereby regulating the cellular levels of target proteins. MiRNAs are initially transcribed by RNA pol II as larger, often polycistronic transcripts and sequentially processed by RNAse III complexes, called Drosha and Dicer to produce the mature miRNA. Many miRNAs show cell- and tissue-specific as well as spatial and temporal expression patterns. There is accumulating evidence that specific miRNAs exert powerful regulation over vascular integrity. In particular it was shown recently that vascular neointimal lesion formation is critically regulated by a set of miRNAs that constitute a restenosis molecular genetic signature. In a related context, miRNAs have been shown to regulate differentiation and pluripotency of embryonic stem cells and may be involved in the plasticity of multipotent cardiac progenitors that we and others have shown can differentiate into cardiac myocytes, vascular smooth muscle cells (VSMCs) and endothelial cells. Disrupted regulation of VSMCs is a central feature of age-associated atherosclerosis. VSMCs are uniquely plastic and oscillate between an elastic and calcified state. The oscillatory property of SMCs may hold the key to new treatments for age-associated vascular abnormalities, including atherosclerosis and restenosis. The data, presented in the examples section which follows, demonstrates that miR-30e regulates the switch of SMCs from the elastic/collagen producing mode to the calcified/bone expressing mode, a process that undoubtedly increases with age.

Modifications of MicroRNA Molecules

As discussed above, the microRNA molecules can be modified by incorporating one or more modified nucleobases, linkages, etc.

Accordingly, in a preferred embodiment, the microRNA comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher $T_m$ (i.e., higher target binding affinity) than; 2'-deoxyoligonucleotides against a given target. The effect of such increased affinity is to greatly enhance microRNA inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis.

In another preferred embodiment, the microRNA is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. MicroRNAs which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. *Acc. Chem. Res.* 1995, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N ($CH_3$)—N($CH_3$)—$CH_2$ and O—N($CH_3$)—$CH_2$—$CH_2$ backbones, wherein the native phosphodiester backbone is represented as O—P—O—CH). The amide backbones disclosed by De Mesmaeker et al. *Acc. Chem. Res.* 1995, 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). MicroRNA molecules may also comprise one or more substituted sugar moieties. Preferred oligonucleotides comprise one of the following at the 2' position: OH, SH, $SCH_3$, F, OCN, $OCH_3$ $OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification also includes 2'-methoxyethoxy [2'-O—$CH_2$ $CH_2$ $OCH_3$, also known as 2'-O-(2-methoxyethyl)] (Martin et al., *Helv. Chim. Acta*, 1995, 78, 486). Other preferred modifications include 2'-methoxy (2'-O—$CH_3$), 2'-propoxy (2'-$OCH_2$ $CH_2CH_3$) and 2'-fluoro (2'-F). Similar modifications may also be made at other positions on the microRNA, particularly the 3' position of the sugar on the 3' terminal nucleotide and the 5' position of 5' terminal nucleotide. MicroRNA molecules may also have sugar mimetics such as cyclobutyls in place of the pentofuranosyl group.

A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include methyl, ethyl, isopropyl, and allyl. A preferred $C_1$ to $C_4$ alkyl group is methyl. An oligoribonucleotide molecule comprising ribonucleotide moieties substituted at the 2' position with a $C_1$ to $C_4$ alkyl group is generally referred to as a 2'-O—($C_1$ to $C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy (alkyloxy) and $C_1$ to $C_4$ alkyl group may comprise any of the alkyl groups described above. One preferred $C_1$ to $C_4$ alkoxy-$C_1$ to $C_4$ alkyl group is methoxyethyl. An oligonucleotide molecule comprising more than one ribonucleotide moiety that is substituted at the 2' position with a $C_1$ to $C_4$ alkoxy-$C_1$ to $C_4$ alkyl group is referred to as a 2'-O—($C_1$ to $C_4$ alkoxy-$C_1$ to $C_4$ alkyl) RNA, e.g., 2'-β-methoxyethyl RNA (MOE RNA).

Another suitable example of a modified ribonucleotide moiety is a ribonucleotide that has a methylene bridge between the 2'-oxygen atom and the 4'-carbon atom. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., *Nucleic Acids Res.* 30, 1911-1918 (2002); Elayadi et al., *Curr. Opinion Invest. Drugs* 2, 558-561 (2001); Orum et al., *Curr. Opinion Mol. Ther.* 3, 239-243 (2001); Koshkin et al., *Tetrahedron* 54, 3607-3630 (1998); Obika et al., *Tetrahedron Lett.* 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. Such 2'-fluororibonucleotide moieties are known in the art. Molecules comprising 2'-fluororibonucleotide moieties are generally referred to herein as 2'-fluororibonucleic acids (FANA). Damha et al., *J. Am. Chem. Soc.* 120, 12976-12977 (1998).

Another modification of the microRNA molecules of the invention involves chemically linking to the microRNA one or more moieties or conjugates which enhance the activity or cellular uptake of the microRNA. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-5-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given compound to be uniformly modified, and in fact more than one of the aforementioned modifications may be incorporated in a single compound or even at a single nucleoside within a microRNA. The present invention also comprises microRNAs, which are chimeric microRNAs. "Chimeric" microRNAs or "chimeras," in the context of this invention, are microRNAs, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

By way of example, RNase H is a cellular endonuclease, which cleaves the RNA strand of RNA:DNA duplex. Activation of RNase H therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric microRNAs of the invention may be formed as composite structures of two or more oligonucleotides, modified oligonucleotides, oligonucleosides and/or oligonucleotide mimetics as described above.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The microRNAs used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the microRNAs is well within the talents of one of ordinary skill in the art. It is also well known to use similar techniques to prepare other microRNAs such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified microRNAs.

In accordance with the invention, use of modifications such as the use of LNA monomers to enhance the potency, specificity and duration of action and broaden the routes of administration of microRNAs comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current microRNAs by LNA monomers. The LNA modified microRNA may have a size similar to the parent compound or may be larger or preferably smaller. It is preferred that such LNA-modified microRNAs contain less than about 70%, more preferably less than about 60%, most preferably less than about 50% LNA monomers and that their sizes are between about 10 and 25 nucleotides, more preferably between about 12 and 20 nucleotides.

Preferred modified microRNA backbones comprise, but not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified microRNA backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred microRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a microRNA mimetic that has been shown to have excellent hybridization properties, is referred to as a peptide nucleic acid (PNA). In PNA compounds, the sugar-backbone of a microRNA is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In a more preferred embodiment of the invention the microRNAs with phosphorothioate backbones and oligonucleosides with heteroatom backbones, and in particular- $CH_2$—NH—O—$CH_2$—, —$CH_2$—N($CH_3$)—O—$CH_2$- known as a methylene (methylimino) or MMI backbone, —$CH_2$—O—N($CH_3$)—$CH_2$—, —$CH_2$N($CH_3$)—N($CH_3$) $CH_2$— and —O—N($CH_3$)—$CH_2$—$CH_2$— wherein the native phosphodiester backbone is represented as —O—P—O—$CH_2$— of the above referenced U.S. Pat. No. 5,489,677, and the amide backbones of the above referenced U.S. Pat. No. 5,602,240. Also preferred are microRNAs having morpholino backbone structures of the above-referenced U.S. Pat. No. 5,034,506.

Other preferred modifications comprise 2'-methoxy (2'-O $CH_3$), 2'-aminopropoxy (2'-O $CH_2CH_2CH_2NH_2$) and 2'-fluoro (2'-F). Similar modifications may also be made at other positions on the microRNA, particularly the 3' position of the sugar on the 3' terminal nucleotide or in 2'-5' linked oligonucleotides and the 5' position of 5' terminal nucleotide. MicroRNAs may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

MicroRNA molecules may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-T7; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Further, nucleobases comprise those disclosed in U.S. Pat. No. 3,687,808, those disclosed in 'The Concise Encyclopaedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications.

Representative United States patents that teach the preparation of the above noted modified nucleobases as well as other modified nucleobases comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the microRNAs of the invention involves chemically linking to the microRNA one or more moieties or conjugates, which enhance the activity, cellular distribution, or cellular uptake of the microRNA.

Such moieties comprise but are not limited to, lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Kabanov et al., *FEBS Lett.,* 1990, 259, 327-330; Svinarchuk et al., *Biochimie,* 1993, 75, 49-54), a phospholipid, e.g., dihexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Mancharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-

237), or an octadecylamine or hexylamino-carbonyl-t oxycholesterol moiety (Crooke et al., *J. Pharmacol. Exp. Ther.*, 1996, 277, 923-937).

Representative United States patents that teach the preparation of such oligonucleotide conjugates comprise, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Formulations and Administration

The microRNA molecules can be introduced into a cell by any method known to those skilled in the art. For example, the microRNA molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges. These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the microRNA oligonucleotide molecules over a prolonged period. The above methods are described in, for example, Hughes et al., *Drug Discovery Today* 6, 303-315 (2001); Liang et al., *Eur. J. Biochem.* 269 5753-5758 (2002); and Becker et al., In Antisense Technology in the Central Nervous System (Leslie, R. A., Hunter, A. J. & Robertson, H. A., eds), pp. 147-157, Oxford University Press.

Targeting of a microRNA molecule to a particular cell can be performed by any method known to those skilled in the art. For example, the microRNA molecule can be conjugated to an antibody or ligand specifically recognized by receptors on the cell. For example, the ligand can be GLP-1 (glucagons-like peptide) which binds GLP-receptors expressed on pancreatic beta-cells. Alternatively, an antibody to GLP-1 can be employed. The effective amount is determined during preclinical trials and clinical trials by methods familiar to physicians and clinicians.

The microRNA molecules can be introduced into the mammal by any method known to those in the art. For example, the above described methods for introducing the molecules into a cell can also be used for introducing the molecules into a mammal.

Other methods include, for example, coating a stent with the microRNA molecules. The molecules can be administered to a mammal by any method known to those skilled in the art. Some examples of suitable modes of administration include oral and systemic administration. Systemic administration can be enteral or parenteral. Liquid or solid (e.g., tablets, gelatin capsules) formulations can be employed. Parenteral administration of the molecules include, for example intravenous, intramuscular, and subcutaneous injections. For instance, a molecule may be administered to a mammal by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a molecule of the present invention can be accomplished by a nebulizer or liquid mist.

The molecules of the present invention can be in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols. The pharmaceutical carrier may also comprise one or more of the following: a stabilizer, a surfactant, preferably a nonionic surfactant, and optionally a salt and/or a buffering agent. The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the molecules.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the molecules of the present invention in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The pharmaceutical carrier may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anesthetic agent such as for example a morphine derivative; or an isotonic agent etc., such as described above. As a further precaution against oxidation or other spoilage, the molecules may be stored under nitrogen gas in vials sealed with impermeable stoppers.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

Embodiments of the invention may be practiced without the theoretical aspects presented. Moreover, the theoretical aspects are presented with the understanding that Applicants do not seek to be bound by the theory presented. It will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1 miR-30e Effects on Gene Expression

Disrupted regulation of vascular smooth muscle cells (VSMCs) is a central feature of atherosclerosis. VSMCs are uniquely plastic and oscillate between a proliferative/migratory and quiescent/differentiated state. This oscillatory property of SMCs may hold the key to new treatments for atherosclerosis by identifying the regulatory molecules. Here it is demonstrated that miR-30e may be such a molecule. miR-30e controls smooth muscle differentiation, migration, and adhesion, all key processes in atherogenesis.

Computational and bioinformatics analysis identified miR-30e as regulator of atherogenesis. Interrogating publicly available gene expression datasets on atherosclerosis, it was found that genes belonging to the cell adhesion gene ontology biological function, such as connexins and thrombospondins, were upregulated in plaque lesions. The 3'UTRs of those genes were studied and it was found that there was an over-representation of a miR-30e binding site in these 3'UTRs. It was hypothesized that there was a common miRNA regulator for these adhesion genes.

Functional Role of miR-30e in Smooth Muscle Cells (SMCs).

It was hypothesized that the downregulation of miR-30e causes the increase in the expression of adhesion genes common to atherosclerosis. miR-30e and a scrambled miR RFP-containing plasmids (Open Biosystems) were packaged into lentivirus and then transduced into SMCs cultured from aortas of 4 wk old male mice. Cnx-43 protein levels were measured by Western Blots (FIG. 1A) and immunocytochemistry in both SMCs and VPCs over-expressing miR-30e (FIGS. 1C-1D) which validated the hypothesis that miR-30e is a regulator of Cnx-43 protein expression. Interestingly, when the mRNA expression levels were quantified, it was found that there was a slight increase in Cnx-43 transcripts rather than a decrease (FIG. 1B) as with the proteins. This may indicate that miR-30e is affecting the translation rather than the transcript degradation of Cnx-43, or that the elevation of Cnx-43 transcripts is part of a homeostatic process triggered by the downregulation of the Cnx-43 protein levels.

To study the effect of miR-30e on global gene expression, microarrays were run. Intriguingly, miR-30e not only downregulated by more than 10 fold ($p<0.05$) adhesion genes, but also inflammation (Mmp3 and Mmp9), cholesterol making and chemokine/migration genes, all key contributors to atherogenesis (FIG. 2). Downregulated by more than 100 fold was CXCL5, which is highly inducible in endothelial and vascular SMCs and is implicated as a marker in congestive heart failure and ischemic stroke. On the other hand, miR-30e upregulated the SMC lineage marker SM22α, evidencing that miR-30e drives the SMCs back to their quiescent differentiated state (FIG. 3). SM22α has an anti-calcification effect in SMCs. In support of an anti-calcification role for miR-30e, the microarrays data also show that miR-30e significantly downregulates the osteogenic transcription factors Runx2 and Bmp2, usually elevated in calcified atherosclerotic vessels.

Statistical Analysis.

For all the experiments described herein, 3 replicates per condition were used and the significance ($p<0.05$ cutoff) was calculated by using an unpaired t-test.

Results:

Functional Role of miR-30e in Smooth Muscle Cells (SMCs).

As described above, the downregulation of miR-30e causes the increase in the expression of adhesion genes common to atherosclerosis. miR-30e or scrambled miR lentivirus was transduced into SMCs cultured from aortas of 4 wk old male mice. Note that SMCs when cultured, even when extracted from healthy mice, become synthetic after few passages. That is, by passage 5, SMCs lose their contractile/differentiated phenotype and become proliferative and migratory. Thus, in the in vitro system, SMCs in passages 5-20, model the pathological state of SMCs. The Cnx-43 protein levels were measured by Western Blots and it was found that indeed Cnx-43 protein, the non-phosphorylated band, was downregulated in the SMCs over-expressing miR-30e relative to the scrambled oligo cells. Also shown by immunocytochemistry that Cnx-43 expression was less in both SMCs and Smooth Muscle Progenitor Cells (SMPCs) that carried the miR-30e lentivirus. Thus, miR-30e is a regulator of Cnx-43 protein expression. Intriguingly, miR-30e also significantly ($p<0.05$) downregulated inflammation, cholesterol making, and chemokine/migration genes, all key contributors to atherogenesis. Downregulated by more than 200 fold and validated by real-time quantitative PCR (qPCR) was the chemokine CXCL5 which is highly induced in endothelial and vascular SMCs and is implicated as a marker in congestive heart failure and ischemic stroke. miR-30e significantly reduced the migration potential of SMCs.

In addition, miR-30e drastically upregulated the SMC lineage markers Calponin (Cnn1), Transgelin (SM22α), Vimentin (Vim), Desmin (Des), Vinculin (Vcl), and Smoothelin (Smtn) evidencing that miR-30e drives the SMCs back to their quiescent differentiated state SM22α is believed to have an anti-calcification effect in SMCs. Moreover, APOE$^{-/-}$ mice lacking SM22α had increased atherosclerotic lesion area and a higher proportion of proliferating SMC-derived plaque cells. In summary, SM22α induction is beneficial for treating atherosclerosis.

Example 2

The Effect of miR-30e in Reducing Carotid Plaque in Atherogenic APOE$^{-/-}$ Mice, with and Without Statin To evaluate the therapeutic effect of miR-30e in vivo, different concentrations of miR-30e will be directly injected into the carotid artery in atherogenic APOE$^{-/-}$ mice±statin, to study plaque dynamics, and determine the optimal dose for reducing plaque. This model is the most accepted model of atherosclerosis. It is noted that the atherosclerotic carotid plaque has been a very successful model for testing drug efficacy in both animal and human subjects.

Functional Role of miR-30e in Atherogenic APOE-/- Mice.

Atherogenic APOE-/- mice were placed on high fat (HF) diet starting at 2 months of age. At 4 months, they were given a dose of miR-30e or scrambled miR lentivirus mixed with pluronic gel and placed on the right carotid artery. 2 months later, the mice were sacrificed, tissue collected and blood serum analyzed. Interestingly, cholesterol and LDL levels were significantly down by 40% and 50% respectively (Table 1). Moreover, hepatic Hmgcr protein levels (the target of Statin) were significantly reduced by 58% (p=0.048) as measured by Western Blot (95 KD band), and aortic fat deposit was reduced by 10% in the aortas as measured by Oil Red staining.

TABLE 1

| APOE-/- on HF | Cholesterol (mg/dL) | Triglycerides (mg/dL) | HDL (mg/dL) | VLDL (mg/dL) | LDL (mg/dL) | Lipidemia Index |
|---|---|---|---|---|---|---|
| Average miR-30e (n = 8) | 520.50 | 125.88 | 103.63 | 25.25 | 389.50 | 1.38 |
| Average scrambled (n = 6) | 841.50 | 88.33 | 100.83 | 17.83 | 722.83 | 2.33 |
| Fold Change | 0.62 | 1.43 | 1.03 | 1.42 | 0.54 | 0.59 |
| p-value | 0.015 | 0.079 | 0.833 | 0.085 | 0.011 | 0.066 |

The above preliminary data evidence that miR-30e is a potent anti-atherogenic molecule that works via regulation of adhesion, VSMC plasticity, and hepatic steroid enzymes.

Non-invasive [and Invasive/Postmortem] Imaging and Quantification of Lesion Size.

Figure 4A:
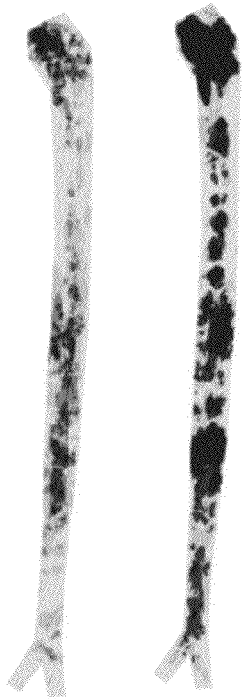
FIG. 4A shows the Oil Red 0 staining of aortas of APOE$^{-/-}$ on normal (left) vs. high fat (right) diet shows increased fat deposit in the high fat diet aorta.
Figure 4B:
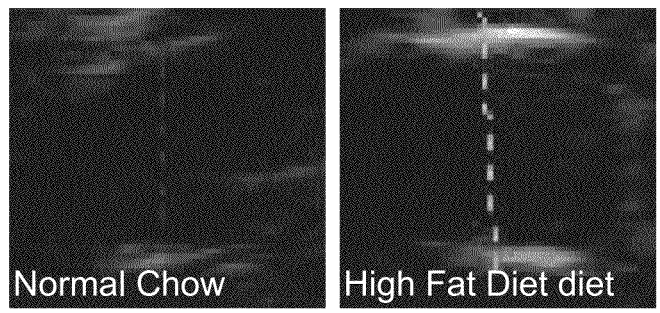
FIG. 4B: a Micro Ultrasound in B-mode similarly shows major thickening of vessel walls at the aortic root when compared to a mouse on normal diet.

Eight-week old APOE$^{-/-}$ C57BL/6 male mice are placed on high fat diet containing 0.15% cholesterol and 21% fat (Research Diets) for 4-5 months. Statistical power=0.9, taking into consideration the animal variability's and possible deaths expected. For non-invasive imaging, micro-ultrasound using Vevo770 system (Visualsonics, Toronto, Canada) is carried out to visualize (as in FIGS. 4A and 4B) and quantify plaque size in the carotids.

Detailed methods of mouse anesthesia, hair removal, B-mode long axis view visualize the plaque length of the carotid, short-axis view to visualize the largest plaque site, optimal freeze-frame image to visualize and measure the external elastic membrane area (EEMA), plaque area, and maximal and minimal intima-medial thickness (IMT), and off-line image analysis are all described (Ni M, et al. *Atherosclerosis*. March 2008; 197(1):64-71).

Measurements are done in triplicate at the same site. Age matched controls on normal chow diet is used to normalize the plaque size. The advantage of this technique is that it records the dynamics of the plaque growth (or regression) over time in each mouse. The acquisition of the time-course of lesion development will be extremely valuable to characterize the dynamics of miR-30e oligonucleotide therapy. A recent study (Ni M et al., 2008) compared the micro-ultrasound imaging to invasive imaging and showed that indeed the micro-ultrasound provides a reliable (and highly correlated) approach to the invasive and quantitative assessment of carotid plaques in APOE-KO mice.

Injections of miR-30e and a Scrambled miR, with and without Statin.

Figure 5:
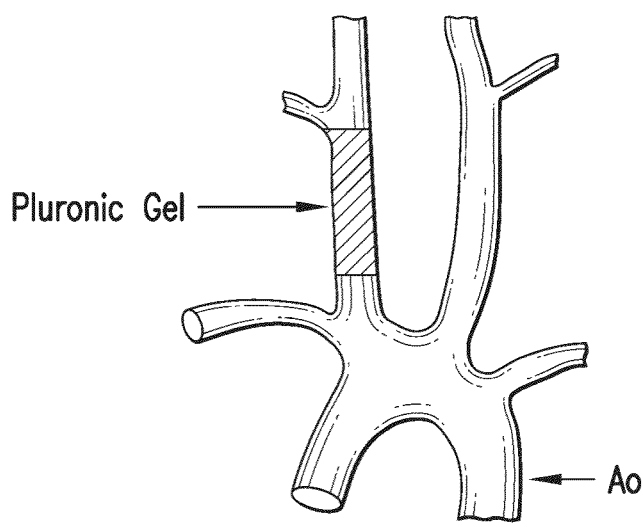
FIG. 5 is a schematic representation showing a pluronic gel containing the miRNA or control lentivirus being injected onto the right carotid artery.

After feeding high fat for 4-5 months to achieve a plaque burden of 35-50% in aortic arch area (20-30% in total aorta area), 25 APOE$^{-/-}$ mice receive miR-30e or scrambled-miR in 1 of 4 doses (40, 50, 60, or 80 mg/kg) via injection onto the external surface of the right carotid artery (see FIG. 5). The injections include the miR lentivirus in 100 µl 20% Pluronic gel F-127 (Sigma) at 4° C., a method shown effective in delivering miRNA to mouse carotid after ligation or in APOE$^{-/-}$ mice (Cordes K R, et al. *Nature*. Aug. 6 2009; 460(7256):705-710; Zernecke A, et al. *Science Signaling*. 2009; 2(100):ra81).

Figure 6:
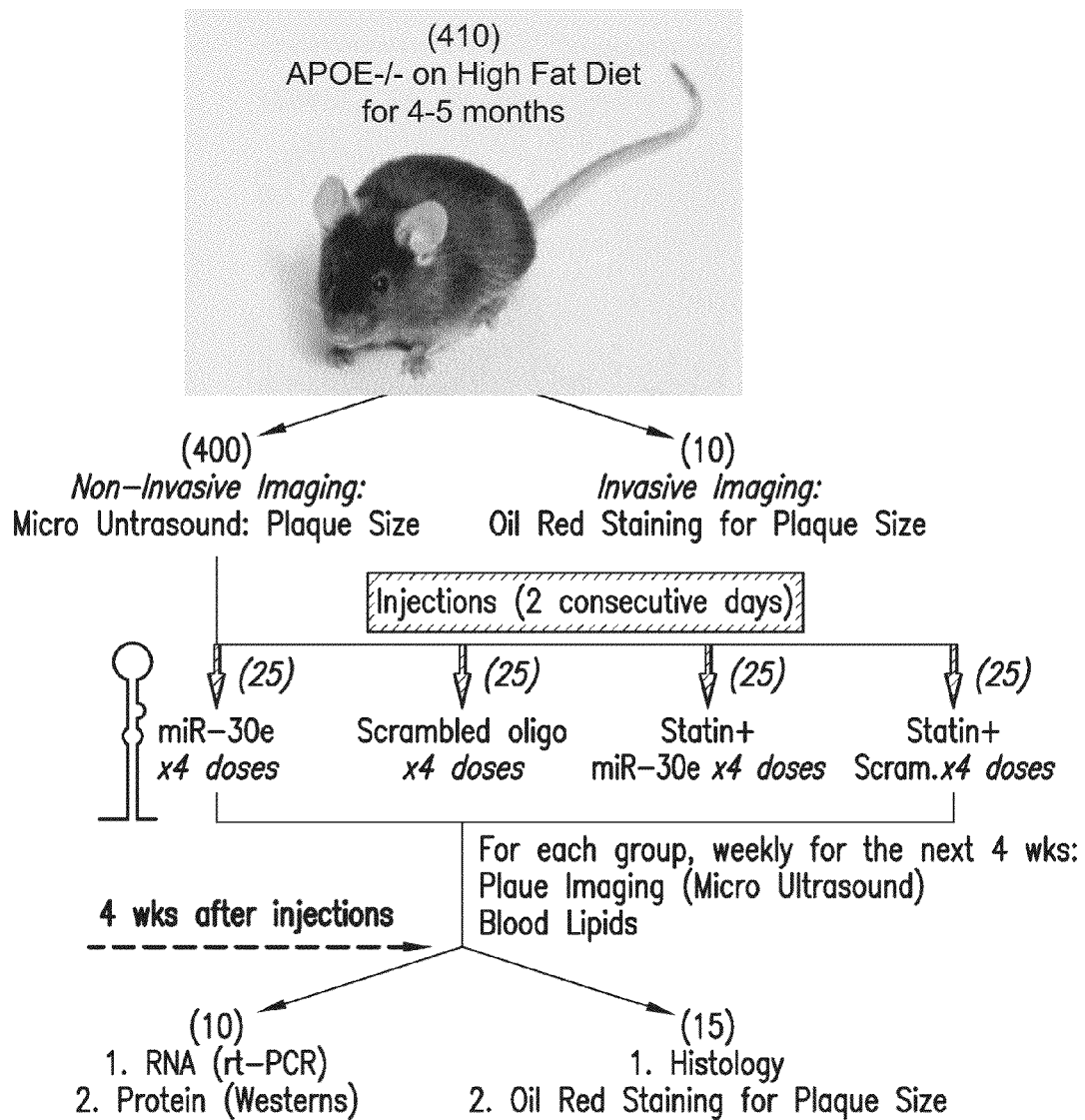
FIG. 6 is a schematic representation showing experimental approach for the in vivo work.

To compare the therapeutic effect of the miR to statin and to explore any additive or synergistic effects, the carotid miR injections are given with or without intraperitoneal (IP) injections of fluvastatin (10 mg/kg) as outlined in FIG. 6. Fluvastatin is administered by IP injection rather than oral lavage to obtain higher accuracy in dose delivery. Both injections are delivered systemically at 1 and 2 days after recordings of the plaque size (as described above) and in parallel, blood samples are collected weekly for serum lipid analyses. Briefly, blood samples are collected from the retro-orbital plexus in 1 mg/ml EDTA, using class capillaries and total cholesterol and triglyceride levels in plasma is measured using standard clinical methods. For the next 4 weeks, carotid plaque will be imaged weekly by micro ultrasound (as shown with the aortas in FIGS. 4A, 4B) and quantified as described above after which mice will be sacrificed, and each group that received a particular injection dosage, will be divided into 2 subgroups, 10 mice for biochemical analysis (RNA and protein), and 15 mice for plaque quantification and histological analyses. It is expected that the ultrasound results will provide guidance as to the optimal effective time of miR±statin on plaque regression.

RNA and Protein Quantification of Adhesion and Cell Migration Molecules.

Injected carotid arteries and contralateral ones are dissected and placed in cold RNA Later solution (Ambion). RT-PCR (TaqMan) and Western blots are used to quantify the levels of the mRNA and proteins of the targets of miR-30e: Cnx-43, Cxcl5, and Cxcl15 (described above). For RT-PCR, a delta delta Ct analysis is employed. For protein quantifications, each gel will have at least 5 replicates and is repeated at least twice. Films are scanned, and bands will be analyzed using Image J. For both RNA and protein quantification, unpaired t-tests are used to calculate significance. A maximum p=0.05 will be accepted.

Compositional Analysis of Atherosclerotic Plaques.

Histology and quantitative immunohistochemistry is used to measure the flowing parameters: plaque area ($\mu m^2$), TUNEL$^+$ cells %, necrotic core$^+$ cells %, plaque cellularity (cells/mm$^2$), VSMC %, macrophage %, medial expansion ($\mu m^2$), stenosis %, and VPCs %. To do this animals are euthanized under $CO_2$, injected carotid arteries and contralateral ones will be dissected and tissues perfused, fixed and stained for specific markers as described (Clarke M C, et al. *Circulation Research*. Jun. 20 2008; 102 (12):1529-1538). For quantitative microscopic morphometry, 15 mice are analyzed via selection of the 4 most representative adjacent sections, resulting in N=14-36 measurements/mouse. Morphometric data is averaged per mouse and these numbers are used to calculate the mean±SEM for each group. TUNEL positive cells are expressed as a % of the total cells (counted by nuclei using H&E staining) in the plaque. Images are captured using a fully automated Leica DMI 6000 inverted microscope. Plaque constituent areas are quantified as number of DABpositive (Mac-3 and αSMA) pixels as a percentage of total plaque pixels. Fibrous caps are defined as the VSMC- and proteoglycan-rich area overlying the cholesterol-rich, matrix-poor, acellular regions of the necrotic cores. Non-specific staining of lipid within the core are excluded from analysis.

Statistical Analysis.

For all the proposed experiments, no less than 7 replicates per condition is used and calculate significance based on p<0.05 cutoff using ANOVA.

Since atherosclerosis is a continuous process that involves repeated healing and injury and based on the preliminary data, it is anticipated that miR therapy using miR-30e injections in atherogenic APOE null mice will have substantial effects in reducing the carotid lesion size, somewhere between 5-12%±6%. The atherosclerosis reduction induced by miR-30e is expected to be mediated through reduction in expression of adhesion, inflammation, chemokine, and steroid-making molecules. A more significant reduction by the miR+statin via synergistic and/or additive mechanisms is also expected based on the preliminary data.

A significant amount of the injected miR-30e virus should be taken by carotid plaque lesion. However, if the virus is not efficiently taken by the plaque, the delivery method is manipulated. For example, injections could be continued for more than just 2 consecutive days, 3-7 days, or a higher concentration of the virus can be tried. If any atherothrombotic events occur, the lentiviral delivery would be switched to custom oligonucleotides with different chemistries of miR-30e, ranging in potency in down-regulating targets.

Another alternative would be to choose an earlier time point in the atherogenic process. Other in vivo models for use in the experiments include, for example, acute models of vascular restenosis such as the balloon injury and stenting mouse models in which vascular remodeling is caused primarily by infiltrating SMCs.

One main goal of the studies is to indentify novel therapeutic strategies. Accordingly, as a future direction, larger preclinical models such as rabbits or swine models will be sued. Other steps include translational strategies to achieve first in human proof of principle studies under FDA auspices.

Example 3 miR-30e as a Regulator of Collagen Repressors

Interrogating publicly available gene expression datasets on vascular aging, it was found that collagens, such as Col3a1 and Col6a3, were downregulated in aortas with age while their repressors, IRF2 and GATA2, were upregulated in aortas with age. The 3'UTRs of those genes were studied and an over-representation of miR-30e binding site in the 3'UTRs of the repressors was found, indicating a common microRNA regulator for these collagen repressors. MiR-30e was significantly downregulated in human failing hearts, in rodent vascular restenosis, and in human platelets during thrombin activation.

Functional Role of miR-30e in Smooth Muscle Cells (SMCs).

Figure 7:
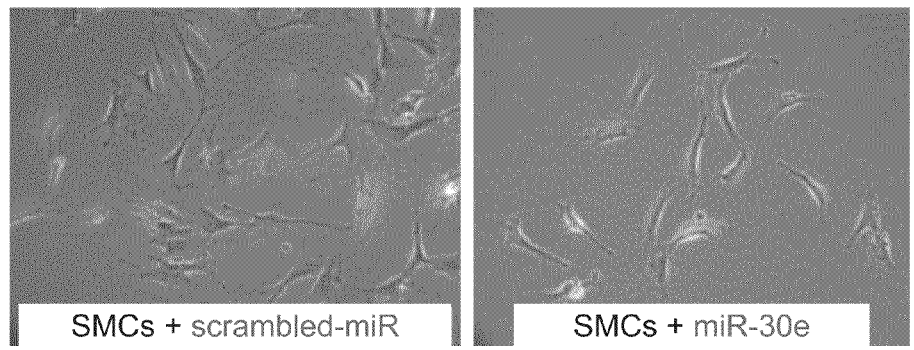
FIG. 7 shows SMCs p15 efficiently transduced with lentivirus-miR-30e or scrambled oligonucleotide.
Figure 8A:
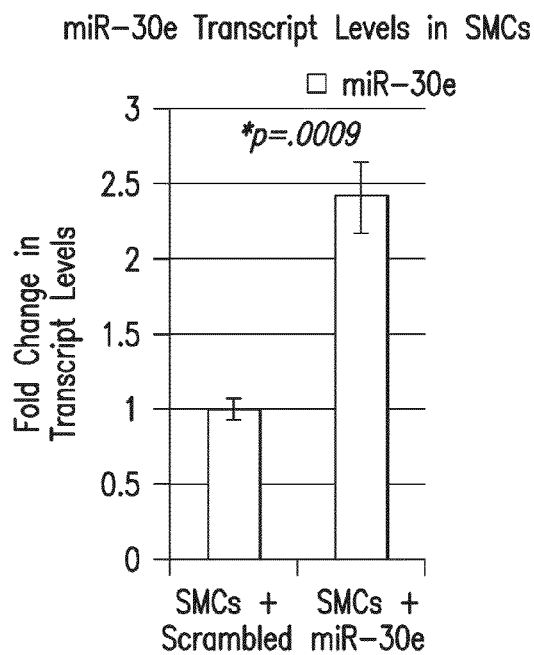
FIGS. 8A and 8B show that miR-30e over-expression in Smooth Muscle Cells (SMCs) p18 causes a significant 2.4 increase in transcript levels of miR-30e (FIG. 8A), and a huge increase in Collagen Type III protein levels (FIG. 8B).
Figure 8B:
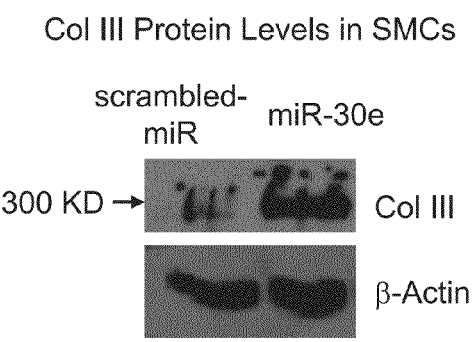

To test the hypothesis that downregulation of miR-30e with age causes an increase in the expression of collagen repressors, miR-30e and a scrambled miR RFP-containing plasmids (Open Biosystems) were packaged into lentivirus and transduced into late passage VSMCs cultured from aortas of 4 wk old male mice. Late passages, starting at p15, were chosen in an attempt to model vascular SMC senescence. SMCs are difficult to transduce. However, by using a double transduction protocol and then cell sorting for RFP+ve cells, efficient transduction (FIG. 7) was achieved. Cells were then collected in Cell Disruption Buffer and each sample was divided in half, for RNA (total and small RNAs) and protein studies, and processed using the Mirvana Paris Kit (Ambion). Col3a1 protein levels were then measured by Western Blots and found that indeed Col3a1 protein expression was upregulated in the SMCs over-expressing miR-30e relative to the scrambled miR cells (FIGS. 8A, 8B). This constituted a first step validation of the hypothesis that miR-30e is a regulator of Col3a protein expression. Further experiments will be directed to the dynamics of this regulation, and the transcript and protein levels of miR-30e targets at several time points will be measured.

Figure 9:
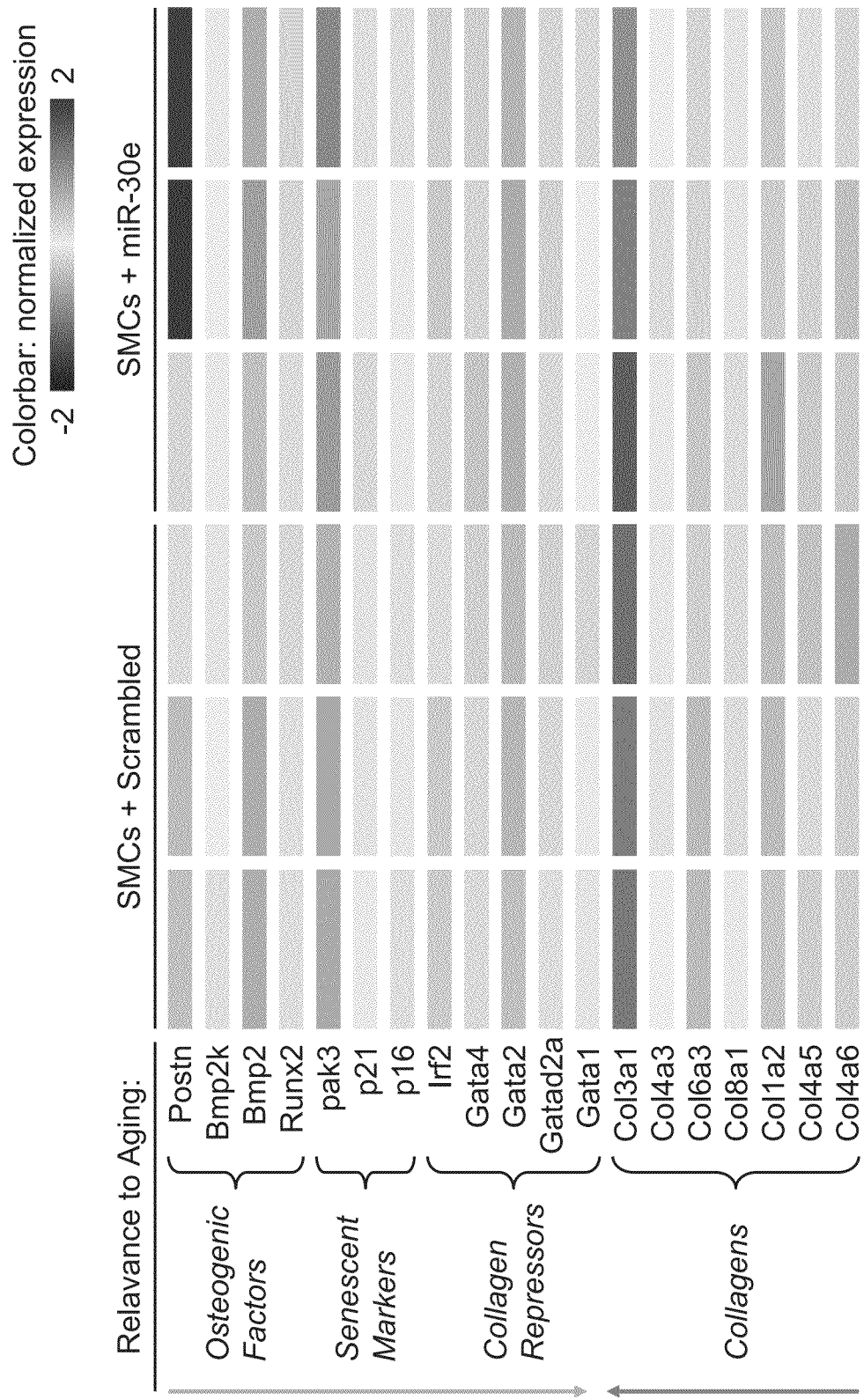
FIG. 9 is a schematic representation showing the gene expression profile from SMCs p18 over-expressing miR-30e vs. a scrambled oligonucleotide (n=3) shows reduction of osteogenic transcription factors, senescent markers, and collagen repressors, and induction of collagens.
Figure 10:
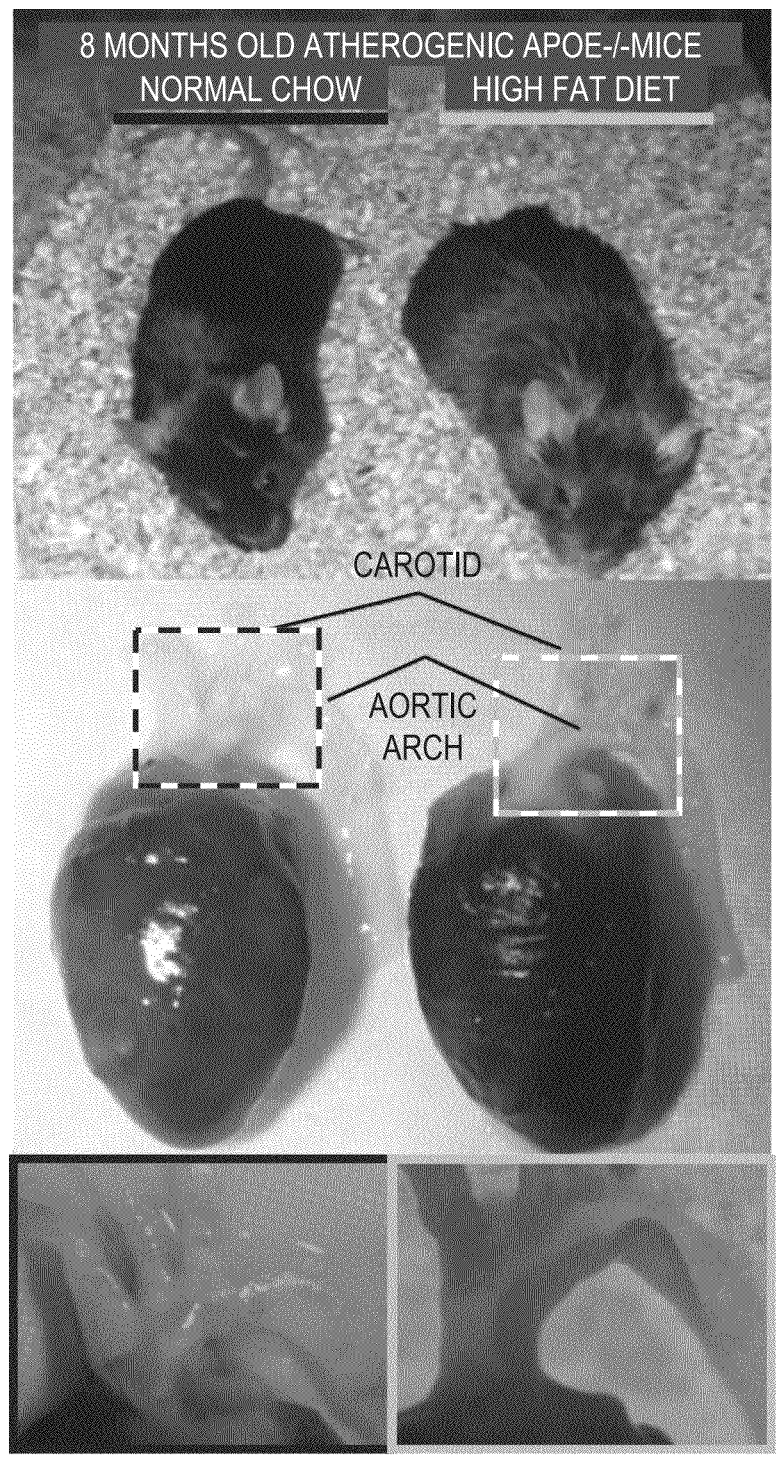
FIG. 10 is a scan of a photograph showing that after 6 months of high fat diet, APOE deficient mice develop significant plaque in the aorta and carotids. Plaque is visible even without staining.
Figure 11:
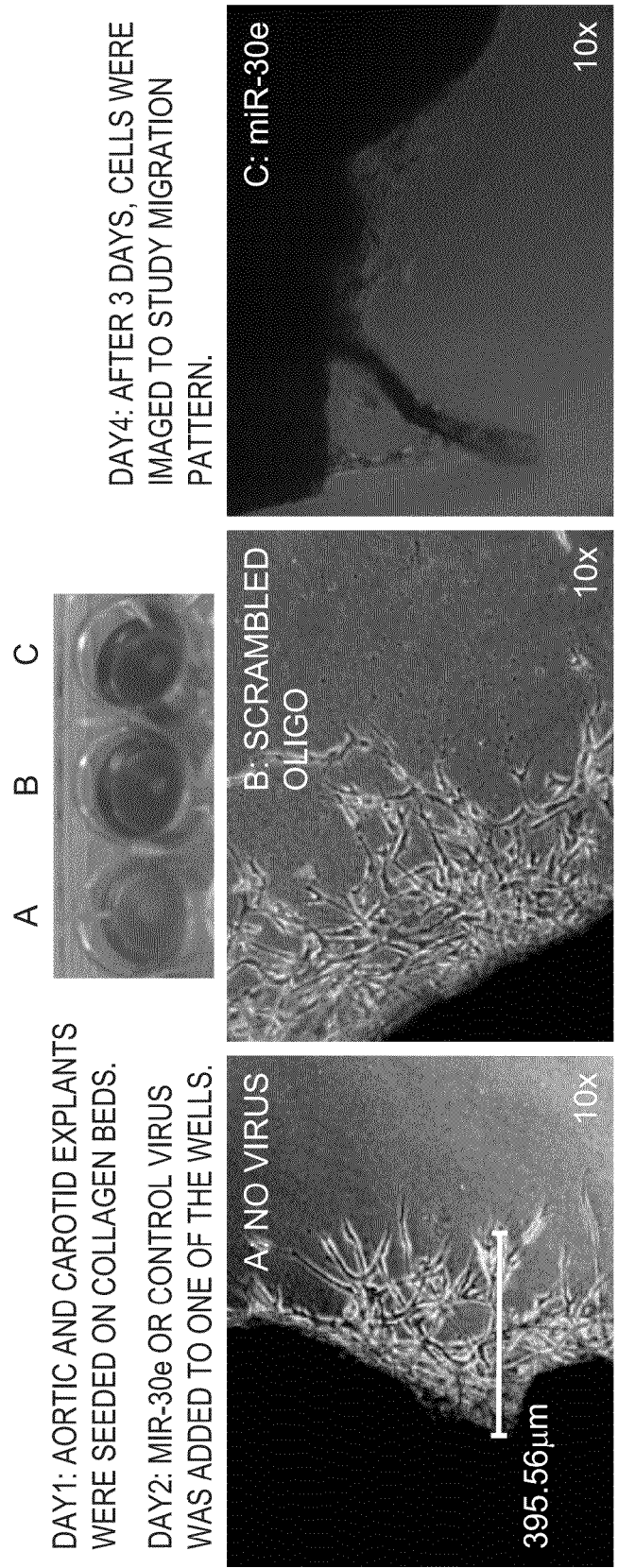
FIG. 11 is a scan of a series of photographs showing results from a 3-day collagen migration assay using explant tissue from aorta and carotid of 8 month atherogenic APOE$^{-/-}$ mice on 6 month high fat diet. Migration of cells to the injured vessel is a major process in atherosclerosis. miR-30e repressed the migration potential of cells within the plaque population. Aorta and carotid fragments from APOE null mice that had been placed on high fat diet for 6 months, were placed on collagen beds. The next day, a virus containing either a scrambled control oligonucleotide or miR-30e were added to wells. After 3 days, pictures of cells migrating from the explants were taken at 10× magnification. At least 10 pictures were taken all around the explant.
Figure 12:
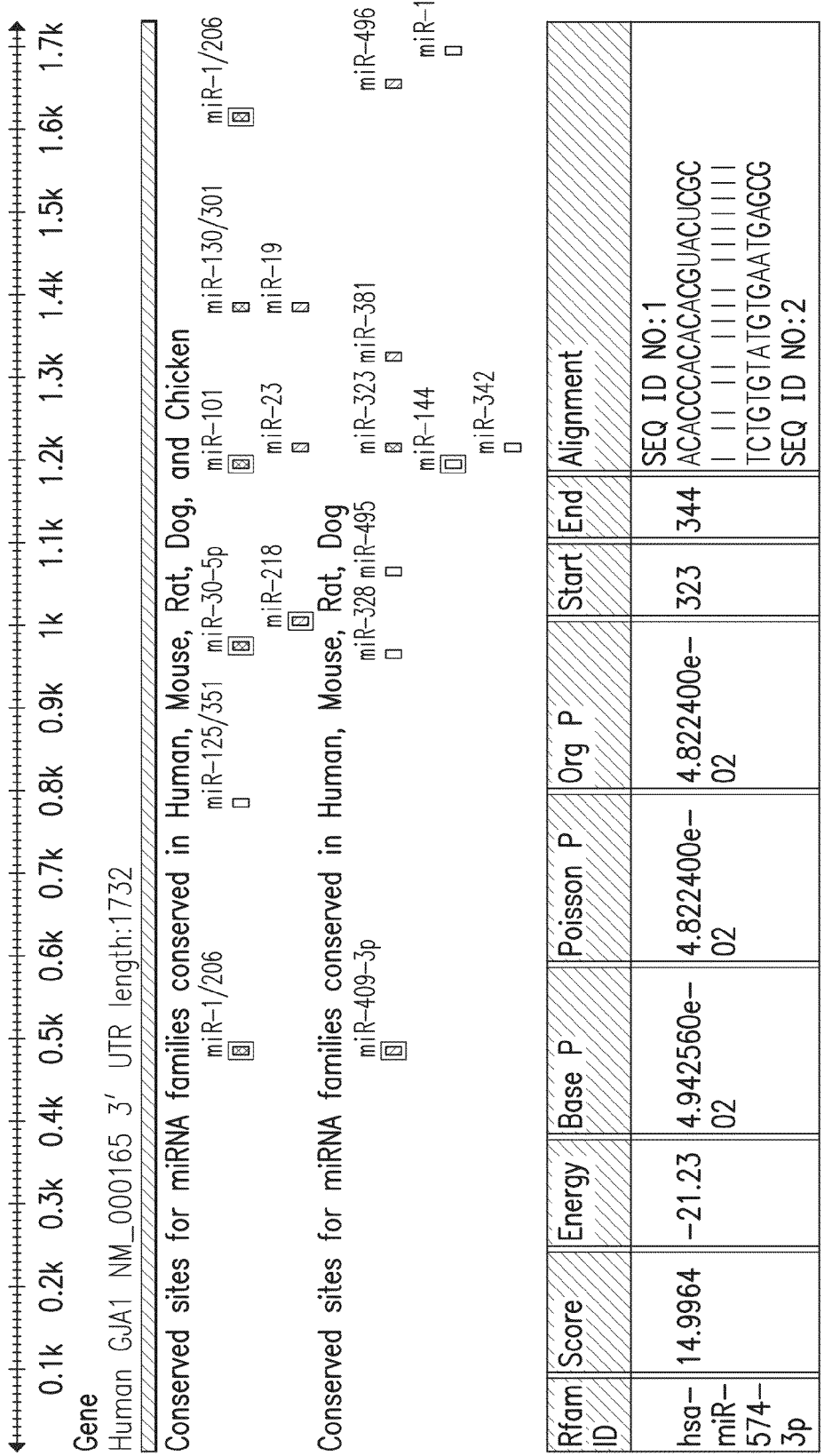
FIG. 12 is a schematic representation showing microRNAs that were predicted to be regulators of Connexin43 (using TargetScan database and miRbase).
Figure 13:
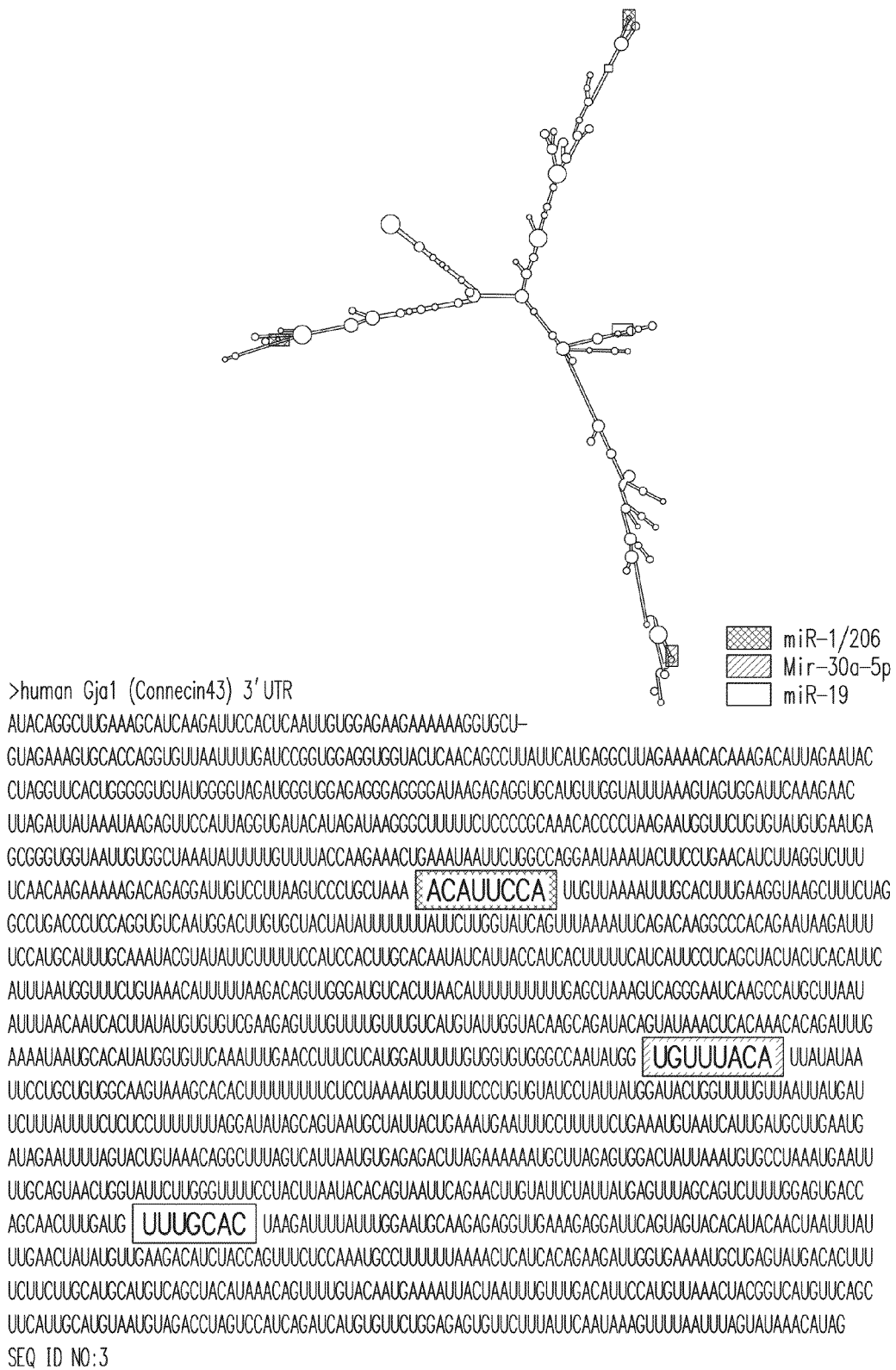
FIG. 13 is a schematic illustration showing the secondary structure of human Gja1/Connexin43 3'-UTR. The secondary structure of the 3' UTR of Connexin43 shows a strong site for miR-1, miR-30, and miR-19.
Figure 14:
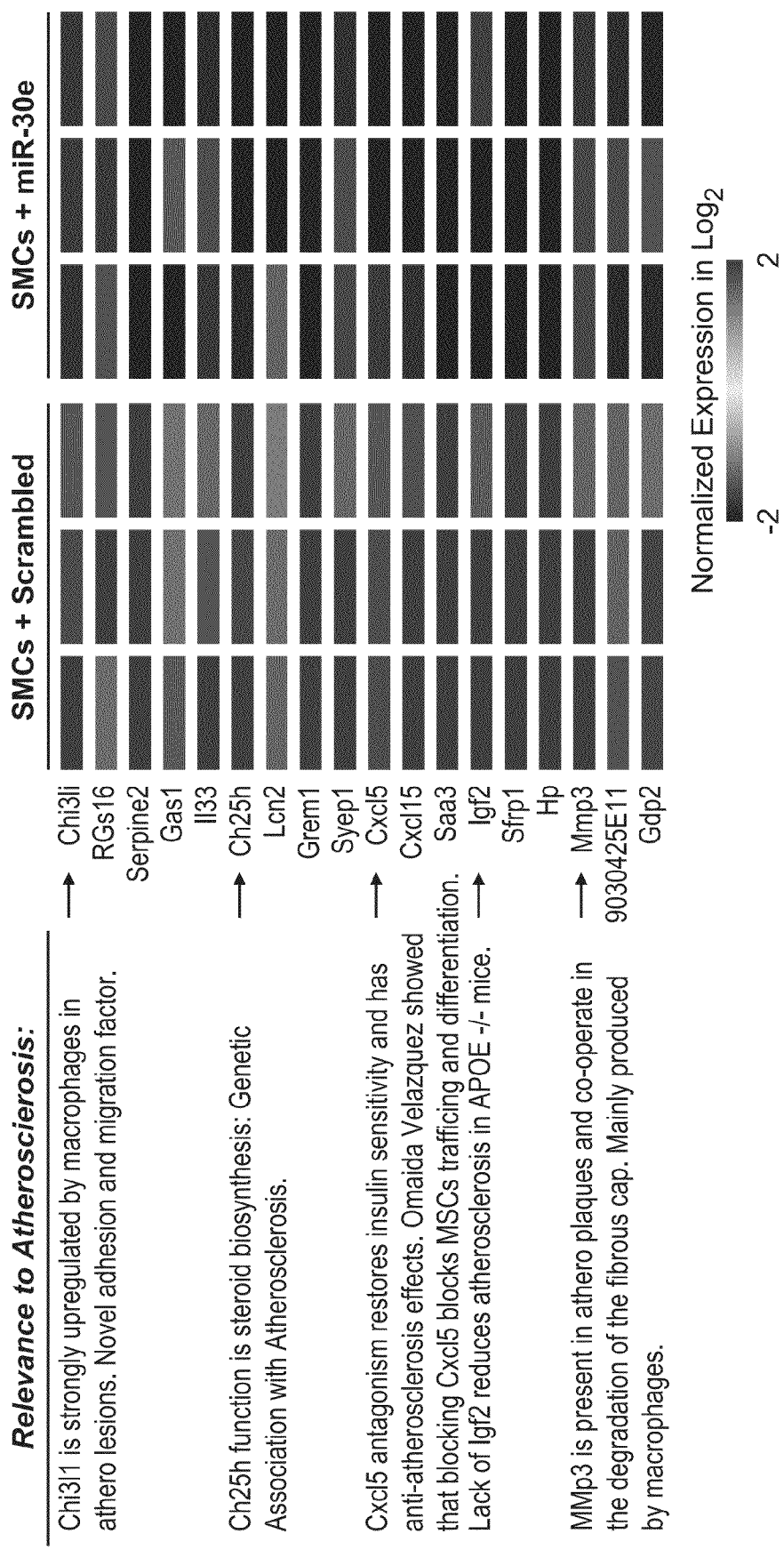
FIG. 14 is a schematic illustration showing the genes which are differentially expressed by a minimum of 10 Fold Change ($p<0.05$) in aortic smooth muscle cells (SMCs) over-expressing miR-30e relative to a scrambled sequence.
Figure 15A:
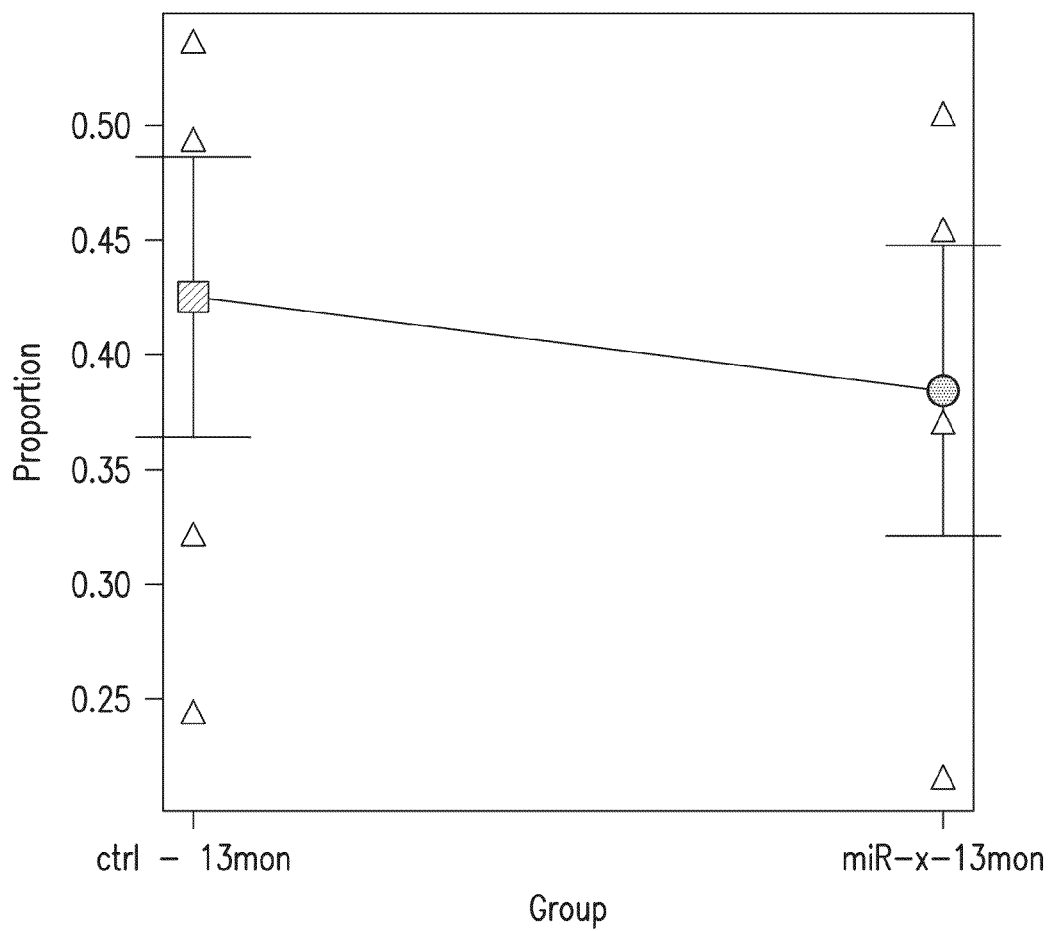
FIG. 15A is a graph showing the proportions of lesion areas detected by Oil Red Staining of whole aortas from 13.5 months old APOE$^{-/-}$ placed on high fat diet and treated with miR-30e via tail vein injection.
Figure 15B:
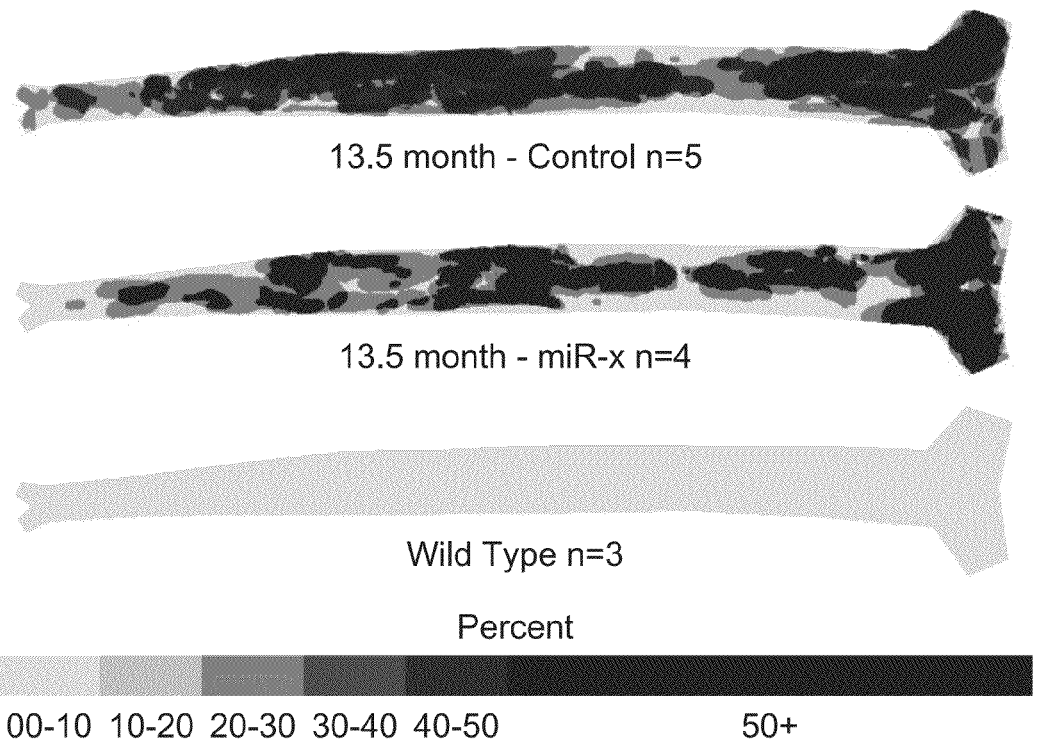
FIG. 15B shows representative images of Oil Red Staining of the aorta of these mice. The results show the reduction of the aortic fat/plaque deposits in the miR-30e treated mice.
Figure 16:
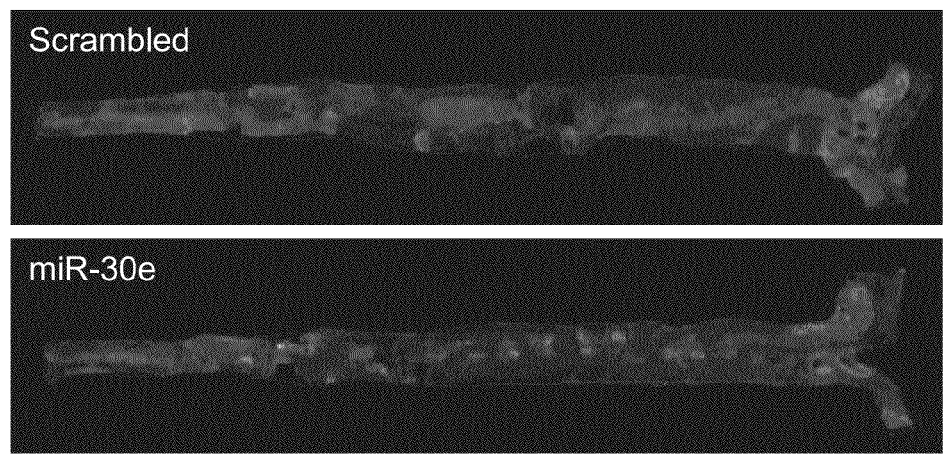
FIG. 16 shows representative images of Oil Red staining of whole aortas from 6 months old APOE$^{-/-}$ mice on high fat diet. The results show about a 10% reduction in fat deposits in aortas after treatment with miR-30e (applied with pluronic gel on the right carorids).
Figure 17:
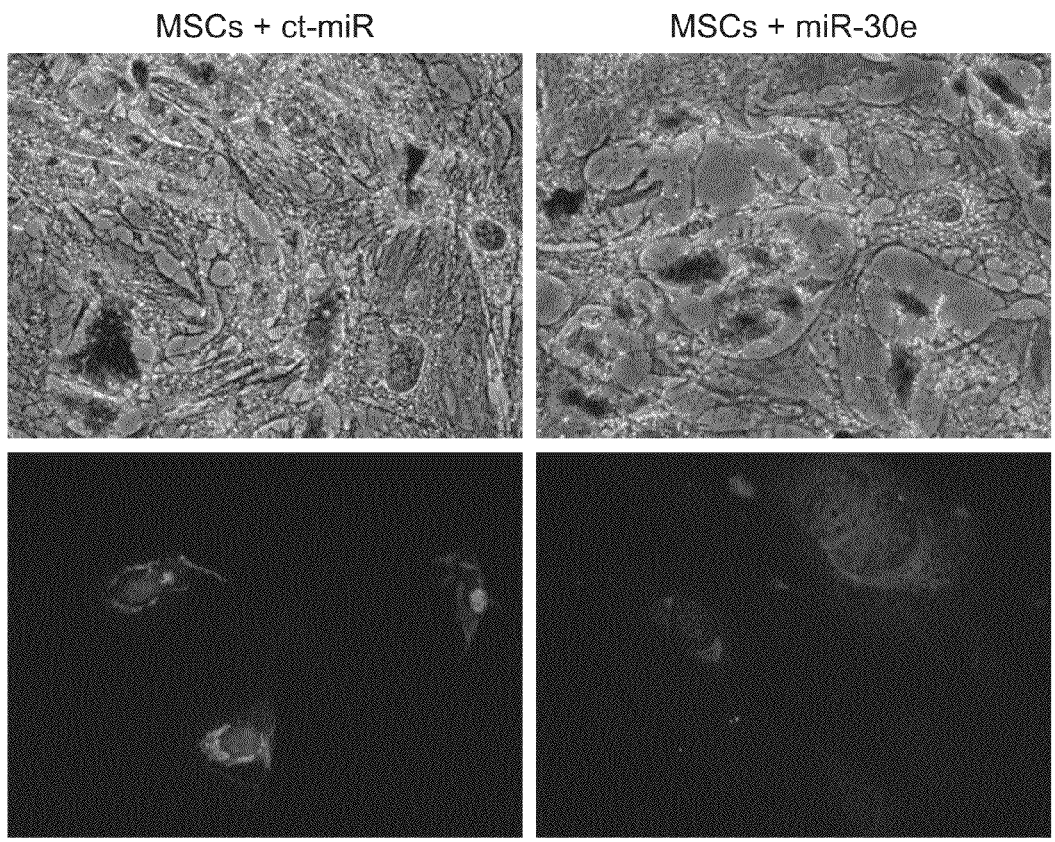
FIG. 17 is a scan of photographs showing the results of regulation of the differentiation potential of mesenchymal stem cells by the microRNA molecules. The upper two panels show the adipogenic differentiation of mesenchymal stem cells by Oil Red staining. The left top panel is with control microRNA (ct-miR) and the right top panel is with miR-30e. The lower two panels show osteogenic differentiation of mesenchymal stem cells and visualized by Spp1 immunostaining. The left lower panel is control microRNA (ct-miR) and the right lower panel is with miR-30e.

To study the effect of miR-30e on global gene expression, RNA samples were measured for hybridization on Affymetrix Mouse Gene ST 1.0 arrays at the University of Miami Gene Expression Core Facility. Intriguingly, miR-30e not only significantly (p<0.05) downregulated the collagen repressors, IRF2, GATA2, and GATA4, but also the osteogenic transcription factors Runx-2, Bmp2, Bmp2k, and Postn, and several senescence markers (p16, p21, and p21-activated kinase3 (pak3); on the other hand, miR-30e induced the expression of several collagen genes, all of which may be key contributors to aging (FIG. 9).

Osteoblasts are differentiated from multipotent mesenchymal cells. This differentiation process is regulated by several cytokines, including bone morphogenetic proteins, transforming growth factor β, Wnt, and hedgehog. Among them, BMP2 (bone morphogenetic protein 2), which is downregulated by miR-30e (FIG. 9), is one of the most powerful cytokines that promote differentiation of mesenchymal cells into osteoblasts in vitro and induce bone formation in vivo. Runt-related gene 2 (Runx2), an essential transcription factor for osteoblast differentiation and bone formation was also targeted by miR-30e (FIG. 9). Aortas from the klotho$^{-/-}$ aging mouse model demonstrate in vivo emergence of osteoblast-like cells expressing RUNX-2 exclusively in the calcified media. BMP2 controls the expression and functions of Runx2 through Smad signaling, forming the BMP2-Smad-Runx2 axis in osteoblastogenesis. miR-30e also drastically repressed the osteoblast specific factor, periostin, Postn (FIG. 9).

Statistical Analysis.

For all the experiments 3 replicates per condition were used significance (p<0.05 cutoff) was calculated by using an unpaired t-test.

Functional Role of miR-30e in Mesenchymal Stem Cells (MSCs).

Adherent MSCs were isolated from 2, 8 and 26 month old mice and characterized as CD45$^-$, Cd11b$^-$, and Sca-1$^+$. Parallel cultures of MSCs, from the 2-month old mice, at passage 25 were grown in MSC or osteogenic differentiation medium for 14 days. Differentiation was confirmed by immunostaining for bone-specific markers. To study the osteogenic/calcification effects of miR-30e on MSCs, a process that happens in age associated vessel calcification, miR-30e or a scrambled oligonucleotide (as described above) were over-expressed in the "young" 2 month MSCs. As described below, the effect of miR-30e on osteogenic differentiation of MSCs from different age groups will be studied.

Example 4

Determining the Role of miR-30e as a Regulator of the Collagen Repressors IRF2 and GATA4 in Aging Vascular Smooth Muscle Cells (SMCs)

Collagens are downregulated with age and are being targeted clinically as anti-aging reagents. It has recently been shown that members of transcription factors IRFs and GATAs repress collagen-1 expression. The data herein show that miR-30e has binding sites in the 3' UTRs of GATA2 and IRF-4 and that over-expression of miR-30e in senescing vascular SMCs, downregulates IRF2, GATA2, and GATA4, and upregulates a group of collagens (FIG. 9).

Methods.

Primary mouse aortic smooth muscle cells will be isolated using standard methods from young (1, 3, and 6 months) and old (18, 22, and 24 months) C57Bl/6 mice (old mice will be purchased from the National Institute of Aging Biological Resources), at least 3 mice per age group, and plated at 70% confluence on fibronectin-coated 60 mm plates using recommended media conditions (DMEM:F12:FBS at 3:1:1). 12-18 hours after plating the cells will be transduced with lentivirus carrying sense (miR-30e) or antisense (antagomiR-30e), both constructs from OpenBiosystems. The cells are then placed in a 37° C. incubator with 5% $CO_2$ and incubated for 48 hours after which the cells are rinsed and collected in Cell Disruption Buffer (Ambion) for RNA and protein studies using a MiRVANA Paris Kit (Abmion). RT-PCR using TaqMan chemistry will be used to quantify miR-30e levels to confirm over-expression and knock down. RT-PCR (TaqMan) and Western blots will be used to quantify the levels of the mRNA and proteins of the predicted targets of IRF2, IRF4, GATA2, and GATA4, as well as the indirect collagen targets, Col3a1, Col4a4, and Col6a3.

Statistical Analysis.

At least n=3 are used per condition. For RT-PCR, a delta delta Ct analysis (control RNA=eukaryotic 18S) is employed to determine the levels of mRNA transcripts. For protein quantifications, each gel will have at least 5 replicates and is repeated at least twice. Films are scanned, and bands are analyzed using Image J. For both RNA and protein quantification, unpaired t-tests with equal variance is used to calculate significance. A maximum p=0.05 will be accepted.

Results: it is thought that there will be a downregulation of the collagen inhibitors, IRFs and GATAs, and an increase in the expression of the collagens, in the SMCs over-expressing miR-30e, both at the transcript and protein levels as seen in FIGS. 8A, 8B and 9. Late passage (p11-18) SMCs from 1-month old mice were used as the model of aging in the preliminary studies. Different expression patterns may be observed in early passage SMCs isolated from young and old mice. Specifically, it is expected that with older ages or with higher passages, SMCs would be in their osteogenic mode. However, the exact age or specific passage number at which SMCs switch from collagen to osteogenic mode is to be determined from the experiments. Finding this transition point in the aging process would have tremendous benefits to understanding the underlying mechanisms in aging vessels and may provide invaluable insights for treating and/or preventing the aging processes.

The role of miR-30e as a Regulator of the Osteogenic Pathway in Mesenchymal Stem:

Cells (MSCs).

Without wishing to be bound by theory, it is hypothesized that aging induces calcification of blood vessels by activating osteogenic pathways in SMCs and MSCs. The data obtained show that in SMCs, over-expression of miR-30e downregulates Runx2, a transcription factor known to drive osteoblastic differentiation and bone formation.

Methods.

Mir-30e or a scrambled oligonucleotide will be over-expressed and knocked down in bone marrow-derived MSCs from young (2 month), adult (18 month) and old (28 month) mice as described above, and the osteogenic markers will be quantified with age. To obtain osteogenic properties, confluent monolayers of each cell group are incubated in osteoblast differentiation media, DMEM-low glucose (Gibco), 10% heat inactivated FBS, 1% penicillin-streptomycin, 10 mM beta-glycerophospate, 0.1 µM dexamethasone, and 0.2 mM ascorbic acid 2-phosphate. The culture media is replaced every 3 days and after 14 days the cells are fixed with 4% paraformaldehyde and stained with Alizarin Red S (Sigma). Control plates are incubated in parallel with DMEM-low glucose supplemented with only 10% heat inactivated FBS and 1% penicillin-streptomycin and subjected to the same processing.

Microscopic pictures are taken using a Zeiss Axio fluorescence microscope and images quantified using Image J. In another method to quantify the effect of miR-30e on the osteogenic differentiation of the MSCs, secreted alkaline phosphates (ALPs) 10-days are measured after exposure to differentiation medium.

Measurement of ALP Activity.

Cellular ALP activity in the cells are visualized by cytochemical staining. After washes with PBS, cells are fixed with citrate-acetone-formaldehyde fixative solution for 15 min. The cells are then washed twice with deionized water and stained for 15 min with an alkaline-dye mixture containing sodium nitrite, FRV-alkaline, and naphthol AS-BI alkaline solutions (Sigma). Quantitative analysis of ALP activity is performed using the SensoLyte pNPP ALP assay kit (AnaSpec, San Jose, Calif.).

Briefly, cells are incubated for 30 min in AP reaction buffer (0.5 ml of 0.75 M 2-amino-2-methyl-1-propanol with 0.5 ml of 2 mg/ml p-nitrophenyl phosphate). The reaction mixture is1 then be mixed with 0.1 NaOH, followed by measurement of optical density at 405 nm. Quantification will also be conducted by real-time PCR and Western blots of the expression levels of the bone-associated proteins osteonectin, osteocalcin, and matrix G1a protein (MGP).

Statistical Analysis.

At least n=3 will be used per condition. For RT-PCR, a delta delta Ct analysis (control RNA=eukaryotic 18S) is employed to determine the levels of mRNA transcripts. For protein quantifications, each gel will have at least 5 replicates and will be repeated at least twice. Films are scanned, and bands are analyzed using Image J. For both RNA and protein quantification, unpaired t-tests with equal variance are used to calculate significance. A maximum p=0.05 will be accepted.

Results:

A progressive decline in alkaline phosphatase secretion with age was found; 26 month MSCs secreted<25% AP relative to 2 month MSCs. A similar pattern of downregulation in the osteogenic pathway was seen at the transcript level with significant decrease in expression of osteogenic markers. Together, these results indicated that the potential for osteogenic differentiation declines with age. The explicit and novel goal of this example, is to determine the role of miR-30e in age-related osteogenesis at several levels.

The results should show a downregulation in the osteogenic potential of MSCs caused by miR-30e and an upregulation with the antagomiR-30e. Over-expression of miR-30e will have a greater effect on old versus young MSCs perhaps reversing the osteogenic phenotype. This will likely implicate miR-30e as a therapeutic target to reduce age-associated calcification. The downregulation of miR-30e should also have a stronger pro-calcification effect in young MSCs because these cells express more endogenous miR-30e. Depending on the initial results the following experiments will also be conducted: comprehensive stage-specific microarray and microRNA profiles of MSC and SMCs during the calcification/collagen deficiency processes respectively, creation of regulatory roadmaps of these processes in this model, and relate them to stage-specific levels of miR-30e. It will also be important to integrate age-related calcification with collagen regulation and miR-30e expression.

Future Experiments:

An understanding of regulatory mechanisms that cause aging in vascular smooth muscle cells (VSMCs) and mesenchymal stem cells will provide valuable insights into age-associated vascular calcification, one of the major underlying cases of morbidity and mortality in our society. There has been very limited research on the role of microRNAs in aging. With the completion of the experiments, there will be an even better understanding of the microRNA-regulated mechanisms by which collagen is reduced in aging cells and by which flexible collagen rich vessels are replaced by stiff bone-rich ones. Since bone-associated proteins such as osteonectin, osteocalcin, and matrix G1a protein have been detected in calcified vascular tissues, calcification is considered to be an organized, regulated process similar to mineralization in bone tissue. While VSMCs are currently thought to be responsible for the formation of vascular calcifications, other subpopulations of cells within the vascular smooth muscle can form osteoblasts; these may include myofibroblasts, mesenchymal stem cells, and endothelial progenitor cells.

Also planned is the investigation and quantification of the osteogenic potential of each sub population and their contribution to vascular calcification. Experiments to investigate other factors including cell-cell interactions (macrophages and VSMCs), lipids, and plasma inorganic phosphate levels that modulate the age-associated calcification process. Moreover, the data shows that miR-30e affects the contractile properties of VSMCs. These highly specialized cells can maintain vascular tonus by contraction or relaxation—a process that is also affected by age. Another goal is to study the effect of miR-30e on age-associated contractility of VSMCs and possibly its relation to vascular/endothelial dysfunction, the forerunners of atherosclerosis and coronary artery disease.

The Abstract of the Disclosure is provided to allow the reader to quickly ascertain the nature of the technical disclosure. It is submitted with the understanding that it will not be used to interpret or limit the scope or meaning of the following claims.

What is claimed:

1. A method of treating a disease or disorder associated with plaque formation, comprising:
   administering to a patient in need thereof, at least one miR-30e or miR-30c molecule in a therapeutically effective amount for reducing Hmgcr protein levels in the patient,
   wherein administration of the at least one miR-30e or miR-30c molecule results in treatment of the disease or disorder associated with plaque formation, and
   wherein the disease or disorder associated with plaque formation is one or both of atherosclerosis and high cholesterol.

2. The method of claim 1, wherein administration of the at least one miR-30e or miR-30c molecule reduces cholesterol levels in the patient.

3. The method of claim 1, wherein the at least one miR-30e or miR-30c molecule is administered to a patient via a stent, vector, liposome, lipid, sugar, or cell-penetrating complex.

* * * * *